(12) United States Patent
Chapman et al.

(10) Patent No.: US 6,627,461 B2
(45) Date of Patent: Sep. 30, 2003

(54) METHOD AND APPARATUS FOR DETECTION OF MOLECULAR EVENTS USING TEMPERATURE CONTROL OF DETECTION ENVIRONMENT

(75) Inventors: Robert G. Chapman, Burlingame, CA (US); John Hefti, San Francisco, CA (US); Barrett J. Bartell, Pacifica, CA (US); Mark A. Rhodes, Redwood City, CA (US); Min Zhao, Foster City, CA (US); Tyler Palmer, San Francisco, CA (US)

(73) Assignee: Signature Bioscience, Inc., San Francisco, CA (US)

( * ) Notice: Subject to any disclaimer, the term of this patent is extended or adjusted under 35 U.S.C. 154(b) by 101 days.

(21) Appl. No.: 09/837,898

(22) Filed: Apr. 18, 2001

(65) Prior Publication Data
US 2002/0155625 A1 Oct. 24, 2002

(51) Int. Cl.[7] ............................................. G01N 33/536
(52) U.S. Cl. ..................... 436/536; 422/82.01; 435/4; 435/6; 435/7.1; 435/7.2; 435/7.92; 435/287.1; 435/287.2; 436/149; 436/150; 436/151; 436/517; 436/518; 436/524; 436/805; 436/806
(58) Field of Search ................... 422/82.01; 435/4, 435/6, 7.1, 7.92, 7.2, 287.1, 287.2; 436/149–151, 517, 518, 524, 805, 806, 536

(56) References Cited

U.S. PATENT DOCUMENTS

| | | | |
|---|---|---|---|
| 4,327,180 A | 4/1982 | Chen | 435/173 |
| 5,025,222 A | 6/1991 | Scott et al. | 324/639 |
| 5,156,810 A | 10/1992 | Ribi | 422/82.01 |
| 5,363,052 A | 11/1994 | McKee | 324/663 |
| 5,653,939 A | 8/1997 | Hollis et al. | 422/50 |
| 5,858,666 A | 1/1999 | Weiss | 435/6 |
| 5,900,618 A | 5/1999 | Anlage et al. | 250/201.3 |
| 5,960,160 A | 9/1999 | Clarke et al. | 392/481 |
| 5,966,017 A | 10/1999 | Scott et al. | 324/639 |
| 6,048,692 A | 4/2000 | Maracas et al. | 435/6 |
| 6,338,968 B1 * | 1/2002 | Hefti | 436/518 |
| 6,368,795 B1 * | 4/2002 | Hefti | 435/6 |
| 6,376,258 B2 * | 4/2002 | Hefti | 436/518 |
| 6,485,905 B2 * | 11/2002 | Hefti | 435/6 |

FOREIGN PATENT DOCUMENTS

EP  0 519 250 A2  12/1992

OTHER PUBLICATIONS

Amo et al., "Dielectric measurements of lysozyme and tri–N–acetyl–D–glucosamine association at radio and microwave frequencies", Biosensors & Bioelectronics, 12(9–10):953–958 (1997).

Colpitts., "Temperature sensitivity of coaxial probe complex permittivity measurements: experimental approach", IEEE Transactions of Microwave Theory and Techniques. 41(2):229–233 (1993).

Esselle et al., "Capacitive sensors for in–vivo measurements of the dielectric properties of biological materials", IEEE Transactions on Instrumentation and Measurement, 37(1):101–105 (1988).

(List continued on next page.)

*Primary Examiner*—Christopher L. Chin

(57) ABSTRACT

The present invention provides a method for detecting a molecular event, comprising (1) applying an electromagnetic test signal to a sample in which a molecular event is being detected, whereby the sample interacts with and modulates the test signal to produce a modulated test signal, and (2) detecting the modulated test signal, wherein the applying and detecting take place in a temperature-controlled environment, wherein the temperature-controlled environment comprises the sample, a radiating portion of a signal generating circuit, and a receiving portion of a signal detection circuit and wherein the applying and detecting take place in the environment at a temperature controlled to within ±0.5° C.

30 Claims, 11 Drawing Sheets

OTHER PUBLICATIONS

Facer et al., "Dielectric spectroscopy for bioanalysis: From 40 Hz to 26.5 GHz in a microfabricated wave guide", Appl. Phys. Lett., 78(7)996–998.

Hefti et al., "Sensitive detection method of dielectric dispersions in aqueous–based, surface–bound macromolecular structures using microwave spectroscopy", Appl. Phys. Lett., 75(12) 1802–1804 (1999).

Hollis et al., "A swept–frequency magnitude method for the dielectric characterization of chemical and biological systems", IEEE, vol. MTT–28, No. 7, Jul. 1980, pp. 791–801.

McKee et al., "Real–time chemical sensing of aqueous ethanol glucose mixtures", IEEE Transactions on Instrumentation and Measurement, vol. 49, No. 1, Feb. 2000, pp. 114–119.

Stuchly et al., "Coaxial line reflection methods for measuring dielectric properties of biological substances at radio and microwave frequencies—A review", IEEE Transactions on Instrumentation and Measurement, vol. IM–29, No. 3, Sept. 1980, pp. 176–183.

Wichaidit et al."Resonant slot antennas as transducers of DNA hybridization: A computational feasibility study", IEEE–MTT, May 2001, MTT Conference in Phoenix, AZ.

* cited by examiner

METHOD AND APPARATUS FOR DETECTION OF MOLECULAR EVENTS USING TEMPERATURE CONTROL OF DETECTION ENVIRONMENT

BACKGROUND OF THE INVENTION

Recent developments in the laboratory of the present inventors have enhanced the ability of researchers to detect molecular events in solution and in real time without requiring molecular labels or extra process steps. The first developments involved a molecular binding layer used to capture potential ligands, with the molecular binding layer being electromagnetically coupled to a continuous transmission line that carried the appropriate electromagnetic signal. See, for example, U.S. application Ser. No. 09/243194, filed Feb. 2, 1999, and U.S. application Ser. No. 09/365578, filed Aug. 8, 1999. This development typically used a signal that did not penetrate deeply into the overlying solution, so that binding interactions could be easily detected regardless of the content of the overlying solution, which was essentially invisible under the experimental conditions (although other embodiments used a molecular binding layer separated from the transmission line). Other techniques directly detected molecular events in solution, using a signal that penetrates into the solution. See, for example, U.S. patent application Ser. No. 09/687,456, filed Oct. 13, 2000.

These new techniques make it possible to detect binding interactions without washing or other separation steps. In other words, it is possible to determine whether A and B, when mixed together, form an A·B complex or simply remain separate from each other but both in the same solution (here denoted A+B). This provides detection and observation of the actual binding event in solution in real time without labels, as opposed to prior art techniques, which are typically capture techniques that detect the result of binding after the event or techniques that require labeling of both components.

Many prior techniques have been able to determine whether A binds with B by capturing B onto a surface to which A is already attached (the surface in effect is a large label attached to A). Such techniques require a washing step prior to the detecting step, as the event actually being detected is the presence of B newly attached to the surface (through binding to A). This "results of binding" orientation of this technique is exemplified by so-called sandwich assays using antibodies and by hybridization of nucleic acids using a probe attached to a surface. Separating unattached B from A attached to the surface allowed the user to tell if B had become bound to A, simply by detecting the presence of B. However, such techniques detect the results of binding and are not detection of the binding event itself in real time, and the attachment of A to the surface can interfere with the ability of A to bind with B and other potential binding partners.

One capture technique that does detect binding in real time is surface plasmon resonance (SPR). This technique uses total internal reflection of light from a surface to which one potential binding partner is attached and detects changes in the critical angle of reflection when a capture event occurs on the surface. They thus are capture devices in requiring attachment of one component to a surface, although they are able to detect binding without wash steps.

Other techniques are available that detect binding in solution in real time, but these techniques typically require labeling of both potential binding partners or binding on a surface. For example, a fluorescent marker can be attached to A while a fluorescent quencher is attached to B. Quenching of fluorescence is an indication of binding. Such techniques, however, are disadvantageous in requiring labeling of one or both the A and B components, which is expensive and which may interfere with the binding event itself.

The newer techniques developed by the present inventors and others working together with them have not only made real-time, label-free binding detection possible (both in solution and on a surface), they also make it possible to provide information on the nature of the binding event. For example, it is possible to determine whether a given test compound binds to the active site on a particular drug receptor as an agonist or an antagonist or whether the test compound binds to an allosteric site, not simply just to indicate whether some uncharacterized binding event has taken place.

In addition to molecular interactions, another type of molecular event that these recent developments have enabled is the study of molecular structures. It is possible, by obtaining an electromagnetic signature of the molecule in the detection range using the now-enabled new techniques, to classify unknown molecules as having structure relationships with know class of molecules (e.g., to classify an unknown molecule as being a G-protein or as having particular features, such as a β-sheet, in its structure).

However, although the promise of the technique has been high, the technology remains in its early stages, and improvements in methodology and equipment are continually needed. For example, early studies were often difficult to duplicate for reasons that—because of the newness of the technology—were not understood.

One of the factors that was considered by the inventors in an attempt to improve reproducibility was control of temperature of the sample, as it is known that the permittivity of a material, such as a test solution, changes with temperature. Such temperature control of the sample, however, did not appear to be sufficient to account for the difficulty in obtaining reproducible results.

It is known already to control temperature of the sample itself (or at least to monitor temperature and to use the temperature to correct experimental values) in an apparatus that determines the permittivity of polar solutions in order to determine the concentration of one polar material (e.g., ethanol) in a second polar material (e.g., water, as might be done in monitoring of a fermentation process). This is exemplified by U.S. Pat. No. 5,363,052 to McKee, entitled "Permittivity Spectroscopy Apparatus and Method." This patent describes an apparatus and method for measuring the permittivity of a polar solution specimen to enable a determination of the concentration of polar constituents in the specimen. The apparatus employs a band pass filter including containment means formed to contain the polar solution and electrically dispose the polar solution as a dielectric element in the band pass filter; conducting means; a source of electrical current connected to said band pass filter; frequency variation means electrically connected to the electric voltage source to enable variation of the frequency at which current is applied to the band pass filter; and voltage sensing means electrically connected to sense the peak voltage passed by the band pass filter. The method includes providing a band pass filter having a conducting microstrip, disposing a specimen solution between the conducting microstrip and the ground plane; applying an electric current to the band pass filter; varying the frequency of the current; and determining the center frequency of the band pass filter as the current is varied.

In this patent, the permittivity of polar solution being investigated and thus the center frequency of the circuit in which the polar solution is an element are a function of temperature. Accordingly, the temperature of the polar solution in the microstrip circuit is controlled. A temperature regulator (temperature control means) of unspecified structure performs this task. A pump circulates polar solution between microstrip assembly and the temperature regulator in order to regulate the temperature of the polar solution at the measurement location.

McKee states that, in practice, maintaining the polar solution at a constant temperature is a difficult task, even with use of a temperature regulator (in fact, there is no description in the patent of the temperature range that the solution would be controlled to within, other than "room temperature" or the "fixed temperature" of a standard permittivity value obtained from a reference source; see, McKee, col. 6, line 8, and col. 7, lines 8–10). McKee therefore proposes an alternative method for compensating for temperature drift by calibrating his microstrip circuit to detect the temperature of polar solution and then calculating permittivity from a formula derived for the particular instrument being used. This is done by measuring the center frequency for the circuit over a range of temperatures and determining an equation from these measurements to relate center frequency to temperature for a given solution.

Even before discovering the McKee patent, applicant had attempted to control variability in measurements by controlling the temperature of the sample and had discovered that control of the sample temperature alone was not sufficient to provide a level of accuracy that allowed routine determination of the occurrence of molecular events. Detection of molecular events is an entirely different process from that of McKee and one that requires much greater accuracy of measurements, since the permittivity changes are much smaller than those obtained when determining the percent composition of mixtures of polar solvents. Specifically, it was found that control of the temperature of a solution being measured via a constant temperature bath, with the solution being transported from the bath location to a second location in which a measurement of electrical parameters is actually being made, did not solve the problem of variable results when attempting to detect molecular events.

Accordingly, there exists a need for further development of the methods of detecting molecular events using the basic technology that originated in the laboratories of the present inventors. The present invention fulfills many of the needs discussed above and others as well, as described herein.

SUMMARY OF THE INVENTION

Surprisingly, it has been discovered that inability to make readily repeatable experimental conclusions, when taking precise electrical parameter measurements for the purpose of detecting molecular events, can be substantially overcome by appropriately controlling temperature of both the sample being measured and the signal transmitting and receiving portions of the electronic circuitry of the detection apparatus, even when control of the temperature of the sample is insufficient. The temperature control must be precise and comprehensive in order to achieve reproducibility. Since a change in electrical measurement parameters can result from the molecular event or from a temperature change, it is difficult if not impossible to determine which event is causing the detected change in the absence of appropriate temperature controls. Correction for temperature via calculation is difficult under many measurement conditions, since different parts of the measurement probe and sample can be at different temperatures in an uncontrolled environment, meaning that calculated temperature corrections based on sample readings do not account for enough error, due to the precision of measurement required when molecular events are being detected. Additionally, one must recall that a temperature probe actually measures its own temperature, and a temperature gradient may exsit between the probe and the material with which it is in contact.

Accordingly, the present invention provides a method for detecting a molecular event, comprising (1) applying an electromagnetic test signal in a frequency range from 1 MHz to 1000 GHz to a sample in which a molecular event is being detected, whereby the sample interacts with and modulates the test signal to produce a modulated test signal, and (2) detecting the modulated test signal, wherein the applying and detecting take place in a temperature-controlled environment, wherein the temperature-controlled environment comprises the sample, a radiating portion of a signal generating circuit, and a receiving portion of a signal detection circuit and wherein the applying and detecting take place in the environment at a temperature controlled to within ±0.5° C.

DESCRIPTION OF THE SPECIFIC EMBODIMENTS

Figure 1:
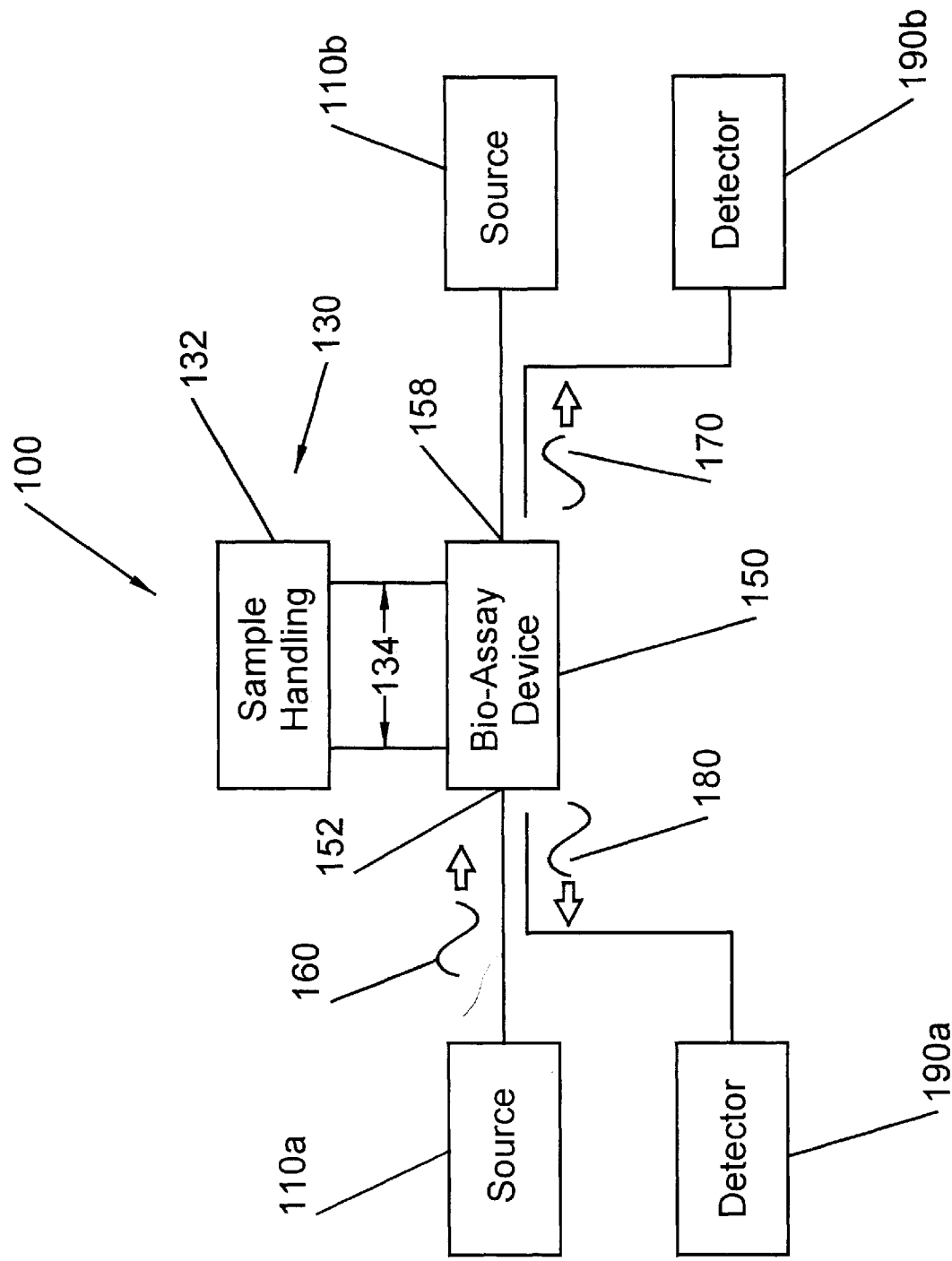
FIG. 1 illustrates a bioassay test system in accordance with one embodiment of the present invention.

Table of Contents
  I. Definition of Terms
  II. General Overview
  III. Bioassay Systems
  IV. Exemplary Temperature Control Systems
  V. Exemplary Methods and Applications VI. Software Implementation
VII. Experiments I. Definition of Terms The following definitions are grouped under subheadings for ease of reference. Inclusion of a definition under one subheading should not be taken as an indication that the definition is limited to structures and events common to that subheading. Any intended limitations on the definitions will be provided by the definitions themselves.

Chemistry and Biologics

As used herein, the term "molecular binding event" (sometimes shortened to "binding event" or "binding") refers to the interaction of a molecule of interest with another molecule. The term "molecular structure" refers to all structural properties of molecules of interest, including the presence of specific molecular substructures (such as alpha helix regions, beta sheets, immunoglobulin domains, and other types of molecular substructures), as well as how the molecule changes its overall physical structure via interaction with other molecules (such as by bending or folding motions), including the molecule's interaction with its own solvation shell while in solution. Together, "molecular structures" and "molecular binding events" are referred to as "molecular events." The simple presence of a molecule of interest in the region where detection/analysis is taking place is not considered to be a "molecular event," but is referred to as a "presence."

Examples of molecular binding events are (1) simple, non-covalent binding, such as occurs between a ligand and its antiligand, and (2) temporary covalent bond formation, such as often occurs when an enzyme is reacting with its substrate. More specific examples of binding events of interest include, but are not limited to, ligand/receptor, antigen/antibody, enzyme/substrate, DNA/DNA, DNA/RNA, RNA/RNA, nucleic acid mismatches, complementary nucleic acids and nucleic acid/proteins. Binding events can occur as primary, secondary, or higher order binding events. A primary binding event is defined as a first molecule binding (specifically or non-specifically) to an entity of any type, whether an independent molecule or a material that is part of a first surface, typically a surface within the detection region, to form a first molecular interaction complex. A secondary binding event is defined as a second molecule binding (specifically or non-specifically) to the first molecular interaction complex. A tertiary binding event is defined as a third molecule binding (specifically or non-specifically) to the second molecular interaction complex, and so on for higher order binding events.

Examples of relevant molecular structures are the presence of a physical substructure (e.g. presence of an alpha helix, a beta sheet, a catalytic active site, a binding region, or a seven-trans-membrane protein structure in a molecule) or a structure relating to some functional capability (e.g., ability to function as an antibody, to transport a particular ligand, to function as an ion channel (or component thereof), or to function as a signal transducer).

Molecular structure is typically detected by comparing the signal obtained from a molecule of unknown structure and/or function to the signal obtained from a molecule of known structure and/or function. Molecular binding events are typically detected by comparing the signal obtained from a sample containing one of the potential binding partners (or the signals from two individual samples, each containing one of the potential binding partners) to the signal obtained from a sample containing both potential binding partners. Together, the detection of a "molecular binding event" or "molecular structure" is often referred to as "molecular detection."

The term "cellular event" refers in a similar manner to reactions and structural rearrangements occurring as a result of the activity of a living cells (which includes cell death). Examples of cellular events include opening and closing of ion channels, leakage of cell contents, passage of material across a membrane (whether by passive or active transport), activation and inactivation of cellular processes, as well as all other functions of living cells. Cellular events are commonly detected by comparing modulated signals obtained from two cells (or collection of cells) that differ in some fashion, for example by being in different environments (e.g., the effect of heat or an added cell stimulant) or that have different genetic structures (e.g., a normal versus a mutated or genetically modified cell). Morpholic changes are also cellular events. The same bioassay systems can be used for molecular and cellular events, differing only in the biological needs of the cells versus the molecules being tested. Accordingly, this specification often refers simply to molecular events (the more difficult of the two measurements under most circumstances) for simplicity, in order to avoid the awkwardness of continually referring to "molecular and/or cellular" events, detection, sample handling, etc., when referring to an apparatus that can be used to detect either molecular events oe cellular events. When appropriate for discussion of a particular event, the event will be described as, for example, a cellular event, a molecular binding event, or a molecular structure determination. When used in a claim, "molecular event" does not include "cellular event" and both are specified if appropriate.

The methodology and apparatuses described herein are primarily of interest to detect and predict molecular and cellular events of biological and pharmaceutical importance that occur in physiological situations (such as in a cellular or subcellular membrane or in the cytosol of a cell). Accordingly, structural properties of molecules or interactions of molecules with each other under conditions that are not identical or similar to physiological conditions are of less interest. For example, formation of a complex of individual molecules under non-physiological conditions, such as would be present in the vacuum field of an electron microscope or in gaseous phase mixtures, would not be considered to be a preferred "molecular binding event," as this term is used herein. Here preferred molecular events and properties are those that exist under "physiological conditions," such as would be present in a natural cellular or intercellular environment, or in an artificial environment, such as in an aqueous buffer, designed to mimic a physiological condition. It will be recognized that local physiological conditions vary from place to place within cells and organisms and that artificial conditions designed to mimic such conditions can also vary considerably. For example, a binding event may occur between a protein and a ligand in a subcellular compartment in the presence of helper proteins and small molecules that affect binding. Such conditions may differ greatly from the physiological conditions in serum, exemplified by the artificial medium referred to as "normal phosphate buffered saline" or PBS. Preferred conditions of the invention will typically be aqueous solutions at a minimum, although some amounts of organic solvents, such as DMSO, may be present to assist solubility of some components being tested. An "aqueous solution" contains at least 50 wt. % water, preferably at least 80 wt. % water, more preferably at least 90 wt. % water, even more preferably at least 95 wt. % water. Other conditions, such as osmolarity, pH, temperature, and pressure, can and will vary considerably in order to mimic local conditions of the intracellular environment in which, for example, a binding event is taking place. The natural conditions in, for example, the cytosol of a cell and a lysosome of that cell, are quite different, and different artificial media would be used to mimic those conditions. Examples of artificial conditions designed to mimic natural ones for the study of various biological events and structures are replete in the literature. Many such artificial media are sold commercially, as exemplified by various scientific supply catalogues, such as the 2000/2001 issue of the Calbiochem General Catalogue, pages 81–82, which lists 60 commercially available buffers with pH values ranging from 3.73 to 9.24 typically used in biological investigations. Also see general references on the preparation of typical media, such as chapter 7 ("The Culture Environment") of *Culture of Animal Cells: A Manual of Basic Techniques,* Third Edition, R. Ian Freshney, Wiley-Liss, New York (1994).

As used herein, the term "analyte" refers to a molecular entity whose presence, structure, binding ability, etc., is being detected or analyzed. Suitable analytes for practice of this invention include, but are not limited to antibodies, antigens, nucleic acids (e.g. natural or synthetic DNA, RNA, gDNA, cDNA, mRNA, tRNA), lectins, sugars, glycoproteins, receptors and their cognate ligand (e.g. growth factors and their associated receptors, cytokines and their associated receptors, signaling molecules and their receptors), small molecules such as existing pharmaceuticals and drug candidates (either from natural products or synthetic analogues developed and stored in combinatorial libraries), metabolites, drugs of abuse and their metabolic by-products, co-factors such as vitamins and other naturally occurring and synthetic compounds, oxygen and other gases found in physiologic fluids, cells, phages, viruses, cellular constituents cell membranes and associated structures, other natural products found in plant and animal sources, and other partially or completely synthetic products.

The word "ligand" is commonly used herein to refer to any molecule for which there exists another molecule (i.e. an "antiligand") that binds to the ligand, owing to a favorable (i.e., negative) change in free energy upon contact between the ligand and antiligand. There is no limit on the size of the interacting substances, so that a ligand (or an antiligand) in this broad sense can consist of either an individual molecule or a larger, organized group of molecules, such as would be presented by a cell, cell membrane, organelle, or synthetic analogue thereof. As used herein, "ligand" and "antiligand" both have this broad sense and can be used interchangeably. However, it is recognized that there is a general tendency in the field of biology to use the word "ligand" to refer to the smaller of the two binding partners that interact with each other, and this convention is followed whenever possible.

As used herein, the term "ligand/antiligand complex" refers to the ligand bound to the antiligand. The binding can be specific or non-specific, and the interacting ligand/antiligand complex are typically bonded to each other through noncovalent forces such as hydrogen bonds, Van der Waals interactions, or other types of molecular interactions.

As used herein, the term "specifically binds," when referring to a protein, nucleic acid, or other binding partner as described herein, refers to a binding reaction which is selective for the ligand of interest in a heterogeneous population of potential ligands. Thus, under designated conditions (e.g., immunoassay conditions in the case of an antibody), the specified antiligand binds to its particular "target" and does not bind in an indistinguishable amount to other potential ligands present in the sample. For example, a cell surface receptor for a hormonal signal (e.g., the estrogen receptor) will selectively bind to a specific hormone (e.g., estradiol), even in the presence of other molecules of similar structure (such as other steroidal hormones, even similar steroids such as estriol). Similarly, nucleic acid sequences that are completely complementary will hybridize to one another under preselected conditions such that other nucleic acids, even those different in sequence at the position of a single nucleotide, hybridize to a lesser extent.

Although measurements described herein are often made on individual molecules or pairs of molecules in solution, at times the method of the invention can be applied to situations in which one of the members of a binding pair is immobilized on a surface while test compounds in solution contact the immobilized molecule (individually, in a mixture, or sequentially). As used herein, when one member of a binding pair is immobilized, the term "antiligand" is usually used to refer to the molecule immobilized on the surface. The antiligand, for example, can be an antibody and the ligand can be a molecule such as an antigen that binds specifically to the antibody. In the event that an antigen is bound to the surface and the antibody is the molecule being detected, for the purposes of this document the antibody can be considered to be the ligand and the antigen considered to be the antiligand. Additionally, once an antiligand has bound to a ligand, the resulting antiligand/ligand complex can be considered an antiligand for the purposes of subsequent binding.

As used herein, the terms "molecule" refers to a biological or chemical entity that exists in the form of a chemical molecule or molecules, as opposed to salts or other non-molecular forms of matter. Many molecules are of the type referred to as organic molecules (compounds containing carbon atoms, among others, connected by covalent bonds), although some molecules do not contain carbon (including simple molecular gases such as molecular oxygen and more complex molecules such as some sulfur-based polymers). The general term "molecule" includes numerous descriptive classes or groups of molecules, such as proteins, nucleic acids, carbohydrates, steroids, organic pharmaceuticals, receptors, antibodies, and lipids. When appropriate, one or more of these more descriptive terms (many of which, such as "protein," themselves describe overlapping groups of compounds) will be used herein because of application of the method to a subgroup of molecules, without detracting from the intent to have such compounds be representative of both the general class "molecules" and the named subclass, such as proteins. When used in its most general meaning, a "molecule" also includes bound complexes of individual molecules, such as those described below. An ionic bond can be present in a primarily covalently bound molecule (such as in a salt of a carboxylic acid or a protein with a metal ion bound to its amino acid residues), and such molecules are still considered to be molecular structures. Of course, it is also possible that salts (e.g., sodium chloride) will be present in the sample that contains a molecular structure, and the presence of such salts does not detract from the practice of the invention. Such salts will participate in the overall dielectric response, but a molecular binding event or property can be detected in their presence. A "molecular binding event" includes the binding of a molecule to an atom or ion, such as in a chelation process (e.g., interation of an iron ion with the heme moiety of hemoglobin).

As used herein, the terms "binding partners," "ligand/antiligand," or "ligand/antiligand complex" refers to pairs (or larger groups; see below) of molecules that specifically contact (e.g. bind to) each other to form a bound complex. Such a pair or other grouping typically consists of two or more molecules that are interacting with each other, usually by the formation of non-covalent bonds (such as dipole—dipole interactions, hydrogen bonding, or van der Waals interactions). The time of interaction (sometimes referred to as the on-off time) can vary considerably, even for molecules that have similar binding affinities, as is well known in the art. Examples include antibody-antigen, lectin-carbohydrate, nucleic acid-nucleic acid, and biotin-avidin pairs. Biological binding partners need not be limited to pairs of single molecules. Thus, for example, a single ligand can be bound by the coordinated action of two or more anti-ligands, or a first antigen/antibody pair can be bound by a second antibody that is specific for the first antibody. Binding can occur with all binding components in solution or with one (or more) of the components attached to a surface and can include complex binding that involves the serial or simultaneous binding of three or more separate molecular entities. Examples of complex binding include GPCR-ligand binding, followed by GPCR/G-protein binding; nuclear receptor/cofactor/ligand/DNA binding; or a binding complex including chaperone proteins, along with a small-molecule ligand. Other examples will be readily apparent to those skilled in the art.

As used herein, the terms "isolated," "purified," and "biologically pure" refer to material which is substantially or essentially free from components that normally accompany it as found in its native state.

As used herein, the term "nucleic acid" refers to a deoxyribonucleotide or ribonucleotide polymer in either single- or double-stranded form, and, unless otherwise limited, encompasses such polymers that contain one or more analogs of natural nucleotides that can hybridize in a similar manner to naturally occurring nucleotides.

As used herein, the terms "polypeptide," "peptide," and "protein" are generally used interchangeably to refer to a polymer of amino acid residues. These terms do not appear to have a consistent use in the art in reference to the size of molecules, although "polypeptide" is often used without regard to size, while "peptides" are smaller than "proteins." Proteins are generally considered to be more complex than simple peptides and often contain material other than amino acids, such as polysaccharide chains. All of these terms apply to polymers containing amino acids in which one or more amino acid residue or peptide bond is an artificial chemical analogue of a corresponding naturally occurring amino acid or bond, as well as to naturally occurring amino acid polymers.

As used herein, the term "enzyme" refers to a protein that acts as a catalyst and reduces the activation energy of a chemical reaction occurring between other compounds or of a chemical reaction in which one compound is broken apart into smaller compounds. The compounds that undergo the reaction under the influence of the enzyme are referred to as "substrates." The enzyme is not a starting material or final product in the reaction, but is unchanged after the reaction is completed.

As used herein, the terms "molecular binding layer" or "MBL" refers to a layer having at least one molecular structure (e.g., an analyte, antiligand, or a ligand/antiligand pair) that is electromagnetically coupled to the signal path. The MBL is typically formed on a fixed surface in the detection region, although mobile surfaces, such as beads or cells, can easily be used along with appropriate fluid movement controls. The molecular binding layer can consist of one or more ligands, antiligands, ligand/antiligand complexes, linkers, matrices of polymers and other materials, or other molecular structures described herein. Further, the molecular binding layer can be extremely diverse and can include one or more components, including matrix layers and/or insulating layers, that have one or more linking groups. The MBL can be electromagnetically coupled to the signal path either via a direct or indirect physical connection or when the ligand is located proximate to, but physically separated from, the signal path. The MBL can be formed on a derivatized surface, such as one having thiol linkers formed from biotinylated metals, all in accordance with standard practice in the art. Sometimes the term "molecular binding region" or "MBR" is used instead of MBL, particularly in cases where the geometry is more complex than a simple layer.

As used herein, the term "linking group" or "linker" refers to a chemical structure used to attach any two components to each other, often on the bioassay device. The linking groups thus have a first binding portion that binds to one component, such as the conductive surface, and a second binding portion that binds to another component, such as the matrix or the antiligand.

Many different molecular events can be evaluated by the method and apparatus described herein. Accordingly, the "components of said molecular event sufficient for said molecular event to occur" can vary greatly, depending on the particular molecular event being detected. For example, the quoted phrase can refer to a single protein when the structure of that protein is being investigated. In a complex binding situation involving a ligand, a protein, and a cofactor, three or more components may be necessary for the binding event to occur (many more, for example, in even more complex binding situation, such as in the formation of a functional ribosome from its component parts). One of ordinary skill in the molecular event under investigation can readily determine the minimum components sufficient for the molecular event to occur, either from prior knowledge or from the detection of a modulated signal that is indicative of binding.

Mechanics and Sample Handling

By "thermal barrier" is meant any physical material that acts to prevent or inhibit heat energy from being transmitted from one region to another, whether by conduction, convection, or radiation. A material that transmits heat energy by one method (e.g., conduction) is still a thermal barrier if it inhibits heat energy transfer by another method (e.g., convection). A preferred thermal barrier has a total thermal conductivity of 50 mW/m.K or less. Examples include polyurethane foam, fiberglass, and acrylic plastic.

"Temperature controller" has its normal meaning and refers to any apparatus that acts to measure and maintain the temperature of a temperature-controlled environment within a desired range.

"Thermal Gain" describes the ability of a temperature-controlled environment or enclosure to isolate the sample, detector, and/or detection electronics from changes in the ambient temperature. The ratio of the change in temperature that occurs in a given time outside the enclosure to the change in temperature that occurs in the same amount of time inside the enclosure is the thermal gain. For example, a 10-degree change in the ambient temperature with a corresponding 1-degree change in temperature-controlled environment constitutes a thermal gain of 10.

As used herein, the term "solution" refers to the resulting mixture formed from a first material (the "solvent," which forms the bulk of the solution) in which a second material (the "solute", such as a target ligand) resides primarily as separate molecules rather than as aggregates of molecules. Solutions can exist in any of the solid, liquid or gaseous states. Solid solutions can be formed from "solvents" made of naturally occurring or synthetic molecules, including carbohydrates, proteins, and oligonucleotides, or of organic polymeric materials, such as nylon, rayon, dacron, polypropylene, teflon, neoprene, and delrin. Liquid solutions include those containing an aqueous, organic or other liquid solvent, including gels, emulsions, and other viscous materials formed from liquids mixed with other substances. Exemplary liquid solutions include those formed from celluloses, dextran derivatives, aqueous solution of d-PBS, Tris buffers, deionized water, blood, physiological buffer, cerebrospinal fluid, urine, saliva, water, and organic solvents, such as ethers or alcohols. Gaseous solutions can consist of organic molecules as gases or vapors in air, nitrogen, hydrogen, or other gaseous solvents. The word "solution" is used herein in many cases to refer to a mixture containing a target ligand and/or antiligand that is being applied to a molecular binding surface. Another example of a solution is the sample that is being analyzed. As previously indicated, liquid solutions, particularly aqueous ones, are preferred for the practice of the invention.

As used herein, the term "test sample" refers to the material being investigated (the analyte) and the medium/buffer in which the analyte is found. The medium or buffer can included solid, liquid or gaseous phase materials; the principal component of most physiological media/buffers is water. Solid phase media can be comprised of naturally occurring or synthetic molecules including carbohydrates, proteins, oligonucleotides, $SiO_2$, GaAs, Au, or alternatively, any organic polymeric material, such as Nylon®, Rayon®, Dacryon®, polypropylene, Teflon®, neoprene, delrin or the like. Liquid phase media include those containing an aqueous, organic or other primary components, gels, gases, and emulsions. Exemplary media include celluloses, dextran derivatives, aqueous solution of d-PBS, Tris, deionized water, blood, cerebrospinal fluid, urine, saliva, water, and organic solvents.

As used herein, a "biological sample" is a sample of biological tissue or fluid that, in a healthy and/or pathological state, is to be assayed for the structure(s) or event(s) of interest. Such biological samples include, but are not limited to, sputum, amniotic fluid, blood, blood cells (e.g., white cells), tissue or fine needle biopsy samples, urine, peritoneal fluid, pleural fluid, and cells from any of these sources. Biological samples also include cells grown in cultures, both mammalian and others. Biological samples further include sections of tissues such as frozen sections taken for histological purposes. Although a biological sample is often taken from a human patient, the meaning is not so limited. The same assays can be used to detect a molecular event of interest in samples from any mammal, such as dogs, cats, sheep, cattle, and pigs, as well as samples from other animal species (e.g., birds, such as chickens or turkey) and plants (e.g., ornamental plants and plants used as foods, such as corn or wheat). The biological sample can be pretreated as necessary by dilution in an appropriate transporting medium solution or concentrated, if desired, and is still referred to as a "biological sample." Any of a number of standard aqueous transporting medium solutions, employing one of a variety of transporting media, such as phosphate, Tris, or the like, preferably at physiological pH can be used. As with biological samples, pretreatment of a more general sample (by dilution, extraction, etc.) once it is obtained from a source material do not prevent the material from being referred to as a sample.

As used herein, the term "fluid reservoir" refers to any location, without regard to physical size or shape, in which the sample fluid is retained prior or subsequent to application of the sample fluid across the detection region. "Fluid reservoir" can refer to a fluid droplet or layer formed on a flat surface and maintained at that location by inertia and/or surface tension. Such arrangements are sometimes used in various "chip" designs commonly used in genomics in which a sample fluid is washed across the surface of a chip that has specific molecular probes (usually DNA fragments of know sequence) attached at known locations on the surface. The "fluid reservoir," however, can be and often is contained within physical walls that restrain movement of the fluid, such as vertical walls that constrain gravitational spreading (as in the side walls of test tube or microtitre plate), completely surrounding walls (as in a sealed container), or partially surrounding walls that direct and/or permit motion in a limited number of directions (such as the walls of a tube or other channel). The last of these named possibilities is often referred to herein as a "fluid channel" and occurs commonly in situations were a fluid is being moved from one location to another (such as in a microfluidics chip) to allow interaction with other samples and/or solutions containing reagents or to allow multiple samples to be transported past a single detection region.

Electronics

As used herein, the term "signal path" refers to a transmission medium that supports the propagation of an electromagnetic signal at the desired frequency of operation. In one embodiment, the signal path consists of a signal plane/ground plane/dielectric substrate structure capable of supporting a transverse electromagnetic (TEM) signal. Exemplary embodiments of this signal path architecture include coaxial cable, microstrip, stripline, coplanar waveguide, slotline, and suspended substrate. Other exemplary architectures include wire, printed circuit board traces, conductive or dielectric waveguide structures, and mutlipolar (e.g., quadrapolar, octapolar) transmission structures. In one embodiment, the signal path includes a single signal port that receives an incident test signal and from which a reflected modulate signal is recovered. In another embodiment, the signal path consists of two or more signal ports: at least one that receives an incident test signal and one that outputs the corresponding modulated test signal.

As used herein, the term "detection region" refers to a region of the bioassay device over which the test sample and signal path are electromagnetically coupled. The detection region may be realized in a variety of forms, e.g., an area within a fluid transport channel located proximate to an open-ended coaxial probe, an area of a flowcell located within a waveguide aperture, or a length of PTFE tubing vertically aligned between the transmission line and ground plane of a microstrip structure to name a few possibilities. The detection region is not limited to any particular volume, but is typically less than 1 ml ($1 \times 10^{-6}$ m$^3$). Smaller detection region volumes such as 1 $\mu$l ($1 \times 10^{-9}$ m$^3$), 1 nl ($1 \times 10^{-12}$ m$^3$), or 1 pl ($1 \times 10^{-15}$ m$^3$) (or ranges between these volumes) are preferable for many of the methods used for testing of binding ability of potential pharmaceutical compounds, because of the small size and expense of the available samples.

As used herein, the term "electromagnetically coupled" refers to the transfer of electromagnetic energy between two objects, e.g., the signal path and molecular events occurring within the test sample. The two objects can be electromagnetically coupled when the objects are in direct contact, (e.g., molecular events occurring in a MBL formed along the surface of a microstrip transmission line), or when the objects are physically separated from each other (e.g., molecular events occurring in solution within a sample that is separated from an open-ended coaxial probe by the wall of a PTFE tube). As a modification, the term "electromagnetically couples" will indicate the interaction of an electromagnetic signal (e.g., the incident test signal) with an object (e.g., molecular events occurring within the test sample).

As used herein, the term "test signal" refers to an ac time-varying signal. In specific embodiments, the test signal is preferably at or above 1 MHz ($1\times10^6$ Hz) and at or below 1000 GHz ($1\times10^{12}$ Hz), such as 10 MHz, 20 MHz, 45 MHz, 100 MHz, 500 MHz, 1 GHz ($1\times10^9$ Hz), 2 GHz, 5 GHz, 7.5 GHz, 10 GHz, 12 GHz, 15 GHz, 18 GHz, 20 GHz, 25 GHz, 30 GHz, 44 GHz, 60 GHz, 110 GHz, 200 GHz, 500 GHz, or 1000 GHz and range anywhere therebetween. A preferred region is from 10 MHz to 110 GHz, a more particularly from 45 MHz to 20 GHz. "Test signal" can refer to a range of frequencies rather than a single frequency, and such a range can selected over any terminal frequencies, including frequency ranges bounded by the specific frequencies named in this paragraph. When referring to the detected range (or multiple) of modulated signals obtained after a range of frequencies has been coupled to a test sample, the term "spectrum" is sometimes used.

By "radiating portion of a signal generating circuit" is meant that portion of a signal path that launches a signal that couples to the sample in the detection region. By "receiving portion of a signal detection circuit" is meant that portion of a signal path that couples to and receives the modulated signal from the detection region of the sample.

It should be noted that the radiating and receiving portions can be part of the same circuit or parts of different circuits. When part of the same circuit, they can be identical (as shown by some of the specific embodiments that follow).

System

As used herein, the term "bioassay device" refers to a structure that incorporates the radiating portion of the a signal generating circuit or the receiving portion of a signal receiving circuit. In an embodiment of the present invention as shown below, a single structure (e.g., a coaxial measurement probe) functions alternatingly as both the radiating and receiving portions of the signal generating/receiving circuits. In the preferred embodiment. In a preferred embodiment, the bioassay device further includes a cavity, recessed area, enclosure, tube, flow cell, or other surface feature or structure that is configured to retain a volume of sample within the detection region of the bioassay device. The bioassay device is not limited to any particular geometry or size, and is defined primarily by the architecture of the signal path and desired volume of the interrogated sample.

By "bioassay system" is meant the overall apparatus, optionally including fluids and/or other materials used as consumables, in which the methods described herein are carried out. The "bioassay system" refers to the bioassay device as described above, in combination with the components necessary to supply and recover the test signals to and from the bioassay device and to analyze the results therefrom. These components can include test equipment (e.g., a network analyzer, vector voltmeter, signal generator, frequency counter, spectrum analyzer), control equipment (e.g., computers, temperature compensation circuitry and components), and sample handling components.

As used herein, the term "matrix" or "binding matrix" refers to a layer of material on the bioassay device that is used as a spacer or to enhance surface area available for binding or to optimize orientation of molecules for enhanced binding, or to enhance any other property of binding so as to optimize the bio-assay device. The matrix layer can be formed from carbohydrates such as dextran, poly amino acids, cross-linked or non-cross linked proteins, and the like.

II. General Overview

The general techniques used with the present invention make use of the observation that molecules can be distinguished and their structural properties and binding abilities measured based upon their dielectric properties in a region of the electromagnetic spectrum not previously used to detect molecular events and/or by using techniques not previously applied to detection of molecular events. These dielectric properties are observed by initially coupling a test signal to a test sample that includes an analyte of interest. The dielectric properties of the analyte modulate the test signal and produce a distinguishable signal response. This response can be recovered, stored, and used to detect and identify the molecule in other test samples. Additionally, interactions of other molecules with the first molecule (e.g., molecular binding events) can also be detected, as the test signal is further modified by the interaction of a second molecule with the first. Detection and identification of molecule properties and of binding events can occur in the liquid, gas, or solid phase, but are preferably carried out in an aqueous physiological environment in order to identify properties of the molecule associated with its function in a biological environment.

The detector assemblies used with the present invention provide a measurement probe operable to couple a test signal to a test sample in which a molecular event is taking place. The test sample is in a fluid reservoir, often a fluid channel or a well of a multiwell plate. A portion of the fluid reservoir, referred to as the detection region, is illuminated with the test signal. The dielectric properties of the molecules involved in the molecular event operate to modulate the test signal, providing a signal having a signal response that is different from the signal response that would be detected if the same test signal were applied to a sample, otherwise identical, that did not contain the molecular event. The signal response is then recovered and provides information about one or more properties of the molecule or molecules involved in the molecular or cellular event under investigation.

In general, the present invention provides a method for detecting a molecular event. The method comprises coupling an electromagnetic test signal in a frequency range from 1 MHz to 1000 GHz to a sample in which a molecular event is being detected, whereby the sample interacts with and modulates the test signal to produce a modulated test signal. The modulated test signal is detected and analyzed to detect the molecular event. It has been found that significant improvements are present when the coupling and detecting take place in a temperature-controlled environment, where the environment comprises the sample, a radiating portion of a signal generating circuit, and a receiving portion of a signal detection circuit. If only the sample (on the one hand) or the electronic components (on the other hand) are temperature controlled, signal analysis is difficult.

Typically, the applying and detecting take place in the environment at a temperature controlled to within $\pm0.5°$ C. Satisfactory results have been obtained in this range, whereas larger temperature ranges have given unsatisfactory results. However, control of temperature to an even greater extent is desired, in order to detect and analyze the signals of molecular events that have relatively smaller electromagnetic signatures. Accordingly, it is preferred to control the temperature of the environment to within $\pm0.05°$ C. or even more preferably to within $\pm0.01°$ C., $\pm0.001°$ C., $\pm0.0001°$ C., or less. Temperature control to within $\pm0.00001°$ C. is obtainable now in zero-gradient crystal ovens, as described in Karlquist et al., "The Theory of Zero-Gradient Crystal Ovens," 1997 IEEE International Frequency Control Symposium, pp. 898–908. Although such precise temperature control (used to control frequency of standard electronic circuitry) has not been used previously in the measurement of biological interactions (because of the lack of need for prior biological operations and the expense associated with temperature control), the existing technology can readily be applied to the bioassay systems of the invention, now that a need has been demonstrated by the present invention to be appropriate for a system in which one is, for example, detecting binding of a ligand with an antiligand and the binding is measured without separating bound from unbound ligand.

Temperature control has been found to be particularly important when the radiating and receiving portions of the circuits comprise a resonant probe, as the resonant frequency can shift markedly with a change in temperature. For example, one embodiment of the invention uses a resonant probe comprising a first coaxial section comprising a longitudinally extending center conductor, a dielectric insulator disposed around the longitudinal axis of the center conductor, and an outer ground plane disposed around the longitudinal axis of the dielectric insulator, the first coaxial section having a probe head and a first gap end, the probe head comprising an open-end coaxial cross section; a second coaxial section comprising a longitudinally extending center conductor, a dielectric insulator disposed around the longitudinal axis of the center conductor, and an outer ground plane disposed around the longitudinal axis of the dielectric insulator, the second coaxial section having a second gap end and a connecting end, the gap end comprising a open-end coaxial cross section and the connecting end comprising a coaxial connector; and a tuning element adjustably engaged between the first and second gap ends and configured to provide a variable gap distance therebetween. All of these parts of the electronic circuitry should be within the temperature-controlled environment, along with the sample. Other examples of configurations that can be used to couple a signal to a sample and that should be included in the temperature-controlled environment are a resonant probe comprising a reentrant cavity, typically used to concentrate signal into the detection region of the sample. Reentrant cavities are well known, as exemplified by Goodwin et al., "Reentrant radio-frequency resonator for automated phase-equilibria and dielectric measurements in fluids," Rev. Sci. Instrumen., 67 (12) 1996, pp. 4294–4303.

Furthermore, the performance of non-resonant probes, such as a non-resonant coaxial probe or transmission line probe, is also improved by the use of a temperature-controlled environment as described herein.

The time period over which the temperature needs to be controlled depends on the timing of the coupling and detection operations. These depend on the particular instrument being used, and there are no limits on the timing, as long as temperature can be controlled during the relevant coupling and detection operations. These operations can be for a single sample or for a set of samples (containing any number of members) whose modulated signals are being compared and analyzed in order to determine whether a molecular event has taken place or not. An example of comparison of signals of a set would be a background signal obtained on buffer, two test samples each containing one member of a potential binding pair, and a test sample containing the mixed potential binding-pair members. It is preferred that all of these samples would be measured with temperature control according to the invention as described herein in order that all the signals could be more readily compared, using techniques described herein and in other applications of this series of applications. When the method is applied to multiple samples, multiple samples in a set of samples are coupled to electromagnetic test signals, thereby producing corresponding modulated test signals that are detected for joint analysis in order to determine one or more molecular event, and coupling and detecting of all samples in the set take place in the temperature-controlled environment. Here a "set of samples" would be minimally those for determination of a single molecular event, but multiple samples could be run sequentially (or concurrently) in order to detect more than one molecular event in a relatively short period of time.

Typical coupling and detecting operations take place over a time period of from 2 seconds to 2 minutes for an individual sample using the instruments available in the laboratories of the inventors, but these should not be taken as limitations on the invention, but as examples of typical operation, unless specifically recited in a claim. When working with multiple samples, coupling and detecting of all samples in a given set typically take place over a time period of from 1 minute to two hours.

As the method is typically applied to biological samples, the size of the temperature-controlled environment need not be large in most cases. Typically a detection operation is carried out on a sample in a fluid reservoir having a detection region with a volume of less than 1.0 mL. Particularly preferred is detection of (1) structural or functional similarity of a first molecular substance to a reference molecular substance or (2) binding of a first molecular substance to a second molecular substance. Such operations are often carried out by (a) introducing a first sample into a fluid channel of a fluid transport system, the fluid transport system having a fluid movement controller and the fluid channel having a sample entry end, a detection region, and a sample exit end, the detection region having a volume of less than 1 mL; (b) causing the sample to move through the channel from the sample entry end toward the sample exit end under the control of the fluid controller; (c) applying a test signal of greater than 10 MHz and less than 1000 GHz to the detection region of the fluid channel; and (d) detecting a change in the test signal as a result of interaction of the test signal with the sample.

Except for the measurement technique, which was developed in the laboratory of the present inventors, the fluid-handling operations are typical of those used in microfluidics operations and other laboratory techniques for manipulating small liquid samples. When using microfluidics, other typical operations include (e) introducing a spacer material into the channel after the first test sample, (f) introducing a further test sample into the channel after the spacer material, (g) causing the further test sample to move through the channel under the control of the fluid controller, whereby a plurality of different test samples separated by spacer material is transported through the channel without intermixing different test samples, and (f) optionally repeating steps (c)–(d) for the further test sample. The spacer material typically comprises a solution of ionic strength sufficiently high to be transported by electroosmotic pumping and the fluid movement controller utilizes electroosmotic pumping of the fluid. Spacers are often a fluid that is substantially immiscible with the test samples and can comprise a gaseous bubble, with the fluid movement controller utilizing physical pumping of the fluid.

Microfluidic systems are often used to handle mixture operations, as well as to move samples from one location to another. A typical mixing operation is carried out by providing a further fluid channel that intersects the first fluid channel in the fluidic transport system. The system provides separate control of fluid movement in the second fluid channel, the second fluid channel containing a test compound or a series of test compounds, to be mixed with sample in the first fluid channel. A test compound from the second fluid channel is mixed with a test sample in the first fluid channel sufficiently upstream from the test signal so that the test compound has time to bind with a molecular structure in a test sample in the first fluid channel before the test sample reaches the test signal.

A preferred embodiment is a method for detecting a molecular event in a test sample in a detection region of a fluid reservoir, the method comprising locating a measurement probe that exhibits a resonant signal response at a predefined frequency in a range from 10 MHz to 1000 GHz proximate to the detection region to electromagnetically couple a signal thereto; supplying a reference medium to the detection region; coupling a test signal to the detection region and recording a baseline signal response; supplying a test sample containing or suspected of containing the molecular event to the detection region; coupling a test signal to the detection region and obtaining a test sample response; determining the difference, if any, between the test sample response and the baseline response; and relating the difference to the molecular event, with temperature being controlled as described elsewhere herein. Use of a measurement probe that exhibits an $S_{11}$ resonant response is preferred in some embodiments.

A preferred technique for coupling a test signal to the detection region and obtaining a baseline signal response comprises generating an incident signal; coupling the incident signal to the detection region; recovering a reflected signal from the detection region; and comparing amplitude or phase of the incident signal to amplitude or phase of the reflected signal. Measurement operations need not be carried out concurrently, so in some embodiments sample measurements are made at different times, followed by comparing a later test sample response with the stored first test sample response.

There are no limitations on the measurement probe used to detect a molecular event in a test sample, provided that the appropriate limitations described and claimed herein are complied with. However, one preferred embodiment of a measurement probe comprises a first coaxial section comprising a longitudinally extending center conductor, a dielectric insulator disposed around the longitudinal axis of the center conductor, and an outer ground plane disposed around the longitudinal axis of the dielectric insulator, the first coaxial section having a probe head and a first gap end, the probe head comprising an open-end coaxial cross section; a second coaxial section comprising a longitudinally extending center conductor, a dielectric insulator disposed around the longitudinal axis of the center conductor, and an outer ground plane disposed around the longitudinal axis of the dielectric insulator, the second coaxial section having a second gap end and a connecting end, the gap end comprising a open-end coaxial cross section and the connecting end comprising a coaxial connector; and a tuning element adjustably engaged between the first and second gap ends and configured to provide a variable gap distance therebetween. Even more preferred is such a probe in which the first section further comprises a shelf conductively attached to the outer conductor and substantially flush with the open end of the probe head.

All of these operations can be carried out in a bioassay system configured to detect a molecular event in a test sample, comprising thermal barriers forming boundaries of a temperature-controlled environment, a temperature controller operably connected to the temperature-controlled environment that controls temperature in the temperature-controlled environment to within ±0.5° C. during a time period in which an environment immediately external to the temperature-controlled environment changes by ±5° C., a radiating portion of a signal generating circuit located in the environment, a sample container located in the environment and positioned to receive an electromagnetic test signal from the radiating portion of the signal generating circuit, whereby sample present in the sample container interacts with and modulates the test signal to produce a modulated test signal, and a receiving portion of a signal detection circuit located in the environment and positioned to receive the modulated signal, where the sample contains a solution or molecular binding layer containing components of the molecular event sufficient for the molecular event to occur. The device can be configured for preferred embodiments of the method that are described above. For example, the sample container can comprise a fluid reservoir, the fluid reservoir comprising a detection region having of volume of less than 1.0 mL. Other preferred embodiments will be apparent from other preferred elements as described herein. A few specific aspects of preferred apparatuses that have not been previously described will be mentioned at this time.

For example, it is not necessary for the entire bioassay system to be within the temperature-controlled environment. In addition to the signal radiating and detecting portions, a signal circuit generally further contains a signal source operable to transmit an electromagnetic incident test signal to the radiating portion of the circuit. Typically, the signal source is located outside the temperature-controlled environment. Examples of a signal source and signal detector in a circuit include a vector network analyzer system, a scalar network analyzer system, or a time domain reflectometer, with the signal being generated outside the controlled-temperature environment and the signal being detected inside the controlled-temperature environment.

Numerous signal detectors are described in the scientific and patent literature but are not sufficiently sensitive to detect the modulation of a signal resulting from a molecular event. Whether a particular signal detector can be used or not can be determined by whether or not the detector operates at a sufficiently high sensitivity to detect that a first modulated test signal is different from a second modulated test signal when the first modulated test signal is obtained while an aqueous sample containing 0.3 μg or less of fibrinogen is present in the detection region and the second modulated test signal is obtained while a second aqueous sample is present in the detection region, the second aqueous sample being identical to the first aqueous sample except that it does not contain any fibrinogen.

Finally, since most analytical instruments in the modem day use internal computer systems to control and analyze data and since signals obtained at different times are often compared, one aspect of the invention is a computer-readable storage medium containing information obtained by the methods as described herein.

III. Bioassay Systems

FIG. 1 illustrates a bioassay test system 100 in accordance with one embodiment of the present invention. The test system 100 includes a signal source 110*a* and a signal detector 190*a* connected to a first port 152 of the bioassay device 150. In this configuration, the signal source and detector can be used to obtain a one-port (i.e., a reflection) signal response. Alternatively, or in addition to the signal detector 190a, the test system 100 may include a signal detector 190b connected a second port 158 of the bioassay device 150. When so configured, the signal source 110a and the signal detector 190b can be used to provide a two-port (i.e., a "through") signal response of the bioassay device 150. A second signal source 110b may be further included to provide a reflection measurement capability at the second port 158 of the bioassay device 150.

The signal sources 110 are operable to generate and launch an electromagnetic signal 160 ("incident test signal") at one or more amplitudes and/or frequencies. The signal detectors operate to recover the test signal after it has interacted with (i.e., after electromagnetically coupling to) the test sample in the bioassay device 150. In a specific embodiment, the signal source 110 and the signal detectors 190 are included within an automated network analyzer, such as model number 8510C from the Hewlett-Packard Company. Other measurement systems such as vector voltmeters, scalar network analyzers, time domain reflectometers, and the like that use signal characteristics of incident, transmitted, and reflected signals to evaluate an object under test may be used in alternative embodiment under the present invention.

The sample handling assembly 130 includes a sample handling device 132 and a sample delivery apparatus 134. The sample handling device 130 may include sample preparation, mixing, and storage functions that may be integrated on a micro-miniature scale using, for instance, a microfluidic platform. The sample delivery apparatus 134 may consist of a tube, etched or photolithographcially formed channel or capillary, or other similar structure that delivers a volume of test sample to a location proximate to the signal path, such that the incident test signal propagating along the signal path will electromagnetically couple to the test sample. Specific embodiments of the sample handling and delivery structures are provided below.

The bioassay device 150 operates as a bioelectrical interface that detects molecular events occurring within the sample using electromagnetic signals. The bioassay device 150 includes a signal path that is configured to support the propagation of electromagnetic signals over the desired frequency range. Electrical engineers will appreciate that the signal path may consist of a variety of different architectures, for instance a waveguide, transverse electromagnetic (TEM) mode structures such as coaxial cable, coplanar waveguide, stripline, microstrip, suspended substrate, and slotline, as well as other structures such as twisted pair, printed circuits, and the like. Specific embodiments of the signal path are illustrated below.

An incident test signal 160 is generated by the signal source 110a and launched along the signal path where it electromagnetically couples from the signal path to the supplied test sample. One or more signal characteristics (amplitude, phase, frequency, group delay, etc.) of the incident test signal 160 are modulated by its interaction with the sample. In a one-port measurement system, a portion of the modulated signal 180 is reflected back along the signal path and recovered by the signal detector 190. In a two-port measurement system, a portion of the modulated signal is transmitted through to the second port and recovered by the second signal detector 190b. The modulation caused by the electromagnetically coupling may consist of a change in the amplitude, phase, frequency, group delay, or other signal parameters.

The modulated test signal 180 (and/or 170) is recovered and its signal characteristics (amplitude, phase, etc.) are compared to signal characteristics of the corresponding incident test signal 160. In a particular embodiment, changes in the amplitude and phase of the modulated reflected signal 180 relative to the incident test signal 160 are computed at each test frequency and a response plotted over the test frequencies as an s-parameter return loss response. In another embodiment, changes in the amplitude and phase of the modulated transmitted signal 170 relative to the incident test signal 160 are computed at each test frequency and a response plotted over the test frequencies as an s-parameter transmission loss response. The signal responses may be used to compute other quantities to further characterize the test sample makeup. Quantities such as impedance, permeability, resonant frequency, and quality factor of resonant structures may also be either measured directly from the measurement system, or computed indirectly therefrom and used as a metric in characterizing the test sample.

Bioassay Devices

Figure 2:
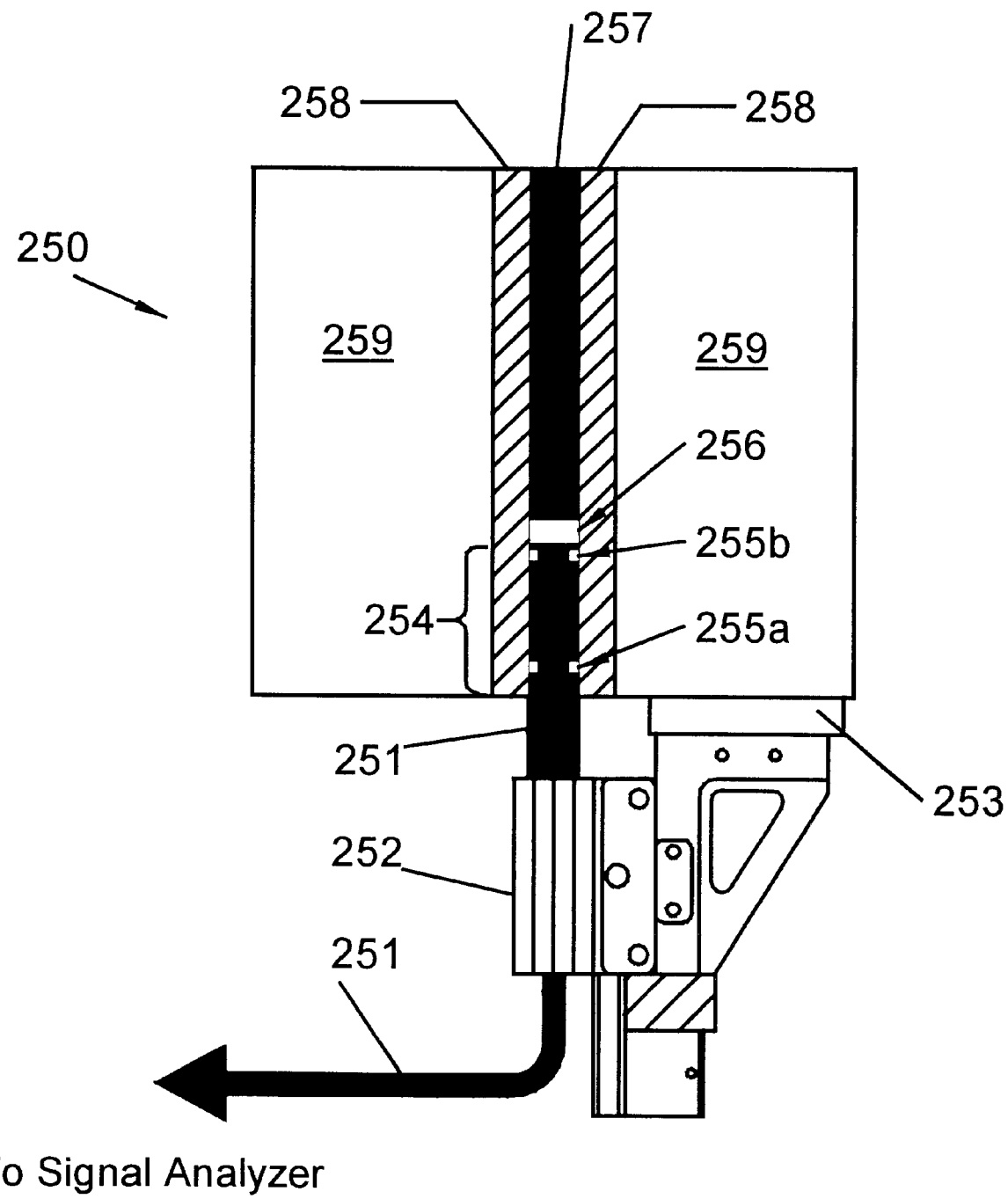
FIG. 2 illustrates a first embodiment of a bioassay device, an open-ended coaxial resonant probe.

FIG. 2 illustrates a first embodiment of the bioassay device 150 shown in FIG. 1, an open-ended coaxial resonant probe 250. The resonant probe 250 includes a first coaxial section 251, a bracket 252, an attachment platform 253, contact rings 255, a tuning gap 256, a second coaxial section 257, a conductive ground tube 258, and a fluidics shelf 259. The first coaxial section 251 is coupled to a signal source and a signal detector illustrated and described below. In one embodiment, the first and second coaxial sections consist of RG401 semi-rigid cable. Those of skill in the art will appreciate that other types of semi-rigid cable as well as other transmission structures can be used in alternative embodiments under the present invention.

Securely held within the bracket 252, the first coaxial section 251 extends into the gap area 254 near the bottom of the fluidics shelf 259. Contact rings 255a and 255b can be optionally attached around the outer surface of the first coaxial section 251 to provide ground conductivity between the first coaxial section 251 and the inner surface of the ground tube 258. In one embodiment, the contact rings are highly conductive springs, although other structures can be used instead. In alternative embodiments, the outer surface of the first coaxial section 251 is brought into contact with the interior surface of the ground tube 258 (copper in one embodiment) to a sufficient degree, thereby obviating the need for the contact rings 255.

The second coaxial section 257 terminates in an open-end and has a length that is approximately one-half of a wavelength ($\lambda/2$) at the desired resonant frequency. In a specific embodiment, the first section 257 is approximately 4 inches, which corresponds to a resonant frequency of 1 GHz. The test sample is supplied at/near the open-end of the second coaxial section 257 such that a signal propagating along the second section 257 is electromagnetically coupled to the test sample. In one embodiment, the test sample comes into direct contact with the open-end cross-section of the second section 257. In another embodiment, the test sample and open-end section are separated by an intervening layer, such as the outer diameter of a fluidic channel or tube. In this instance, the intervening layer is sufficiently signal transparent to permit electromagnetic coupling through the intervening layer to the test sample. Occurrence of a molecular event may be detected either in "solid phase" by using probes immobilized over the detection region surface to bind to predefined targets in the solution, or in "solution phase" in which mobile molecular events occur over the detection region.

The first and second coaxial sections 251 and 257 are separated by a tuning gap 256 that electrically operates to fine-tune the resonant response to the desired frequency. In the illustrated embodiment, the second coaxial section 257 is secured within the ground tube 258 within the fluidics shelf 259. The first coaxial section 251 is inserted into the gap region 254, the outer surface of the first coaxial section 251 making electrical contact with the interior surface of the ground tube 258, thereby providing a continuous ground potential therebetween. The tuning gap 256 formed between the first and second coaxial sections 251 and 257 is made either shorter or longer by moving the bracket 252 either up or down, respectively. The reader will appreciate that the position of the second coaxial section 257 within the conductive ground tube 258 can be adjustable, either alternatively or in addition to the first coaxial section 251. The attachment platform 253 attaches to and holds stationary the fluidics shelf 259, allowing the bracket to either insert or remove the first coaxial section 251 therefrom. In a specific embodiment, the bracket 252 is motor driven and included within a precision motorized translational stage assembly available from the Newport Corporation of Irvine, Calif.

Figure 3:
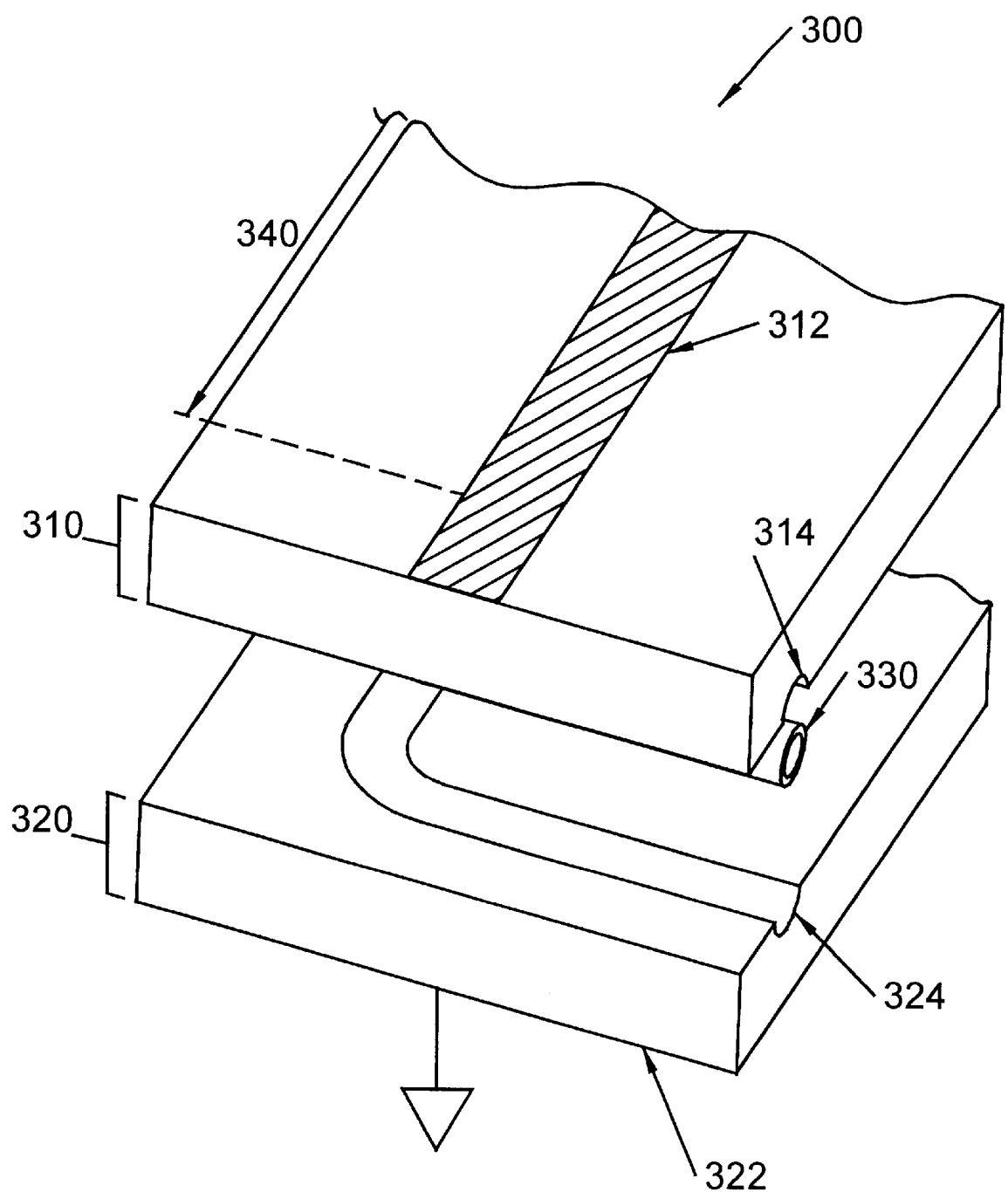
FIG. 3 illustrates a second embodiment of the bioassay device, a broadband microstrip detector.

FIG. 3 illustrates a second embodiment of the bioassay device, a broadband microstrip detector. The microstrip detector 300 includes top and bottom dielectric plates 310 and 320 and a flow tube 330 interposed therebetween. Top and bottom dielectric plates 310 and 320 are preferably constructed from a material exhibiting a low loss tangent at the desired frequency of operation. In the illustrated embodiment, the dielectric plates 310 and 320 are each 0.030" thick of GML 1000 (available from Gil Technologies of Collierville, Tenn.) having a relative dielectric constant of approximately 3.2. In one embodiment, flow tube 330 is constructed from a material having a low loss tangent and a smooth, resilient surface morphology that inhibits analyte formation along the inner surface and detection of molecular events occur in solution phase as they move along the detection length 340 of the device. In another embodiment, the flow tube 330 may include immobilized probes on the inner surface which are operable to capture predefined targets occurring within the test sample. A PTFE tube having an ID of 0.015" and OD of 0.030" is used in the illustrated embodiment, although other materials and/or sizes may be used as well.

The top dielectric plate 310 includes a transmission line 312 deposited on the top surface and a channel 314 formed on the bottom surface. The width of transmission line 312 is chosen to provide a predetermined characteristic impedance along the detection length 340 (further described below). The impedance calculation may take into account the varying dielectric constants and dimensions introduced by channels 314 and 324 and flow tube 330. The transmission line 312 is typically formed from gold or copper.

The second dielectric plate 320 includes a channel 324 formed on the top surface and metallization deposited on the bottom surface. The channel 324 is aligned with channel 314 to form a cavity within which the flow tube 330 extends. The metallization 322 deposited on the bottom surface functions as the ground plane of the microstrip detector and will typically consist of a highly conductive material such as gold or copper. Channels 314 and 324 are aligned to form a cavity that retains the flow tube 330 in a substantially vertically aligned position between the transmission line 312 and the ground plane 322. The flow tube is held between the transmission line 312 and the ground plane 322 along the detection length 340. This configuration results in the passage of a significant number of field lines emanating from the transmission line through the flow tube (and accordingly, the test sample) before terminating on the ground plane 322. The dielectric properties of the molecular events within the sample will modulate the signal propagating along the transmission line 312 (i.e., by altering the field lines setup between the transmission line 312 and ground plane 322), thereby providing a means to detect and identify the molecular events occurring in the test sample.

Figure 4:
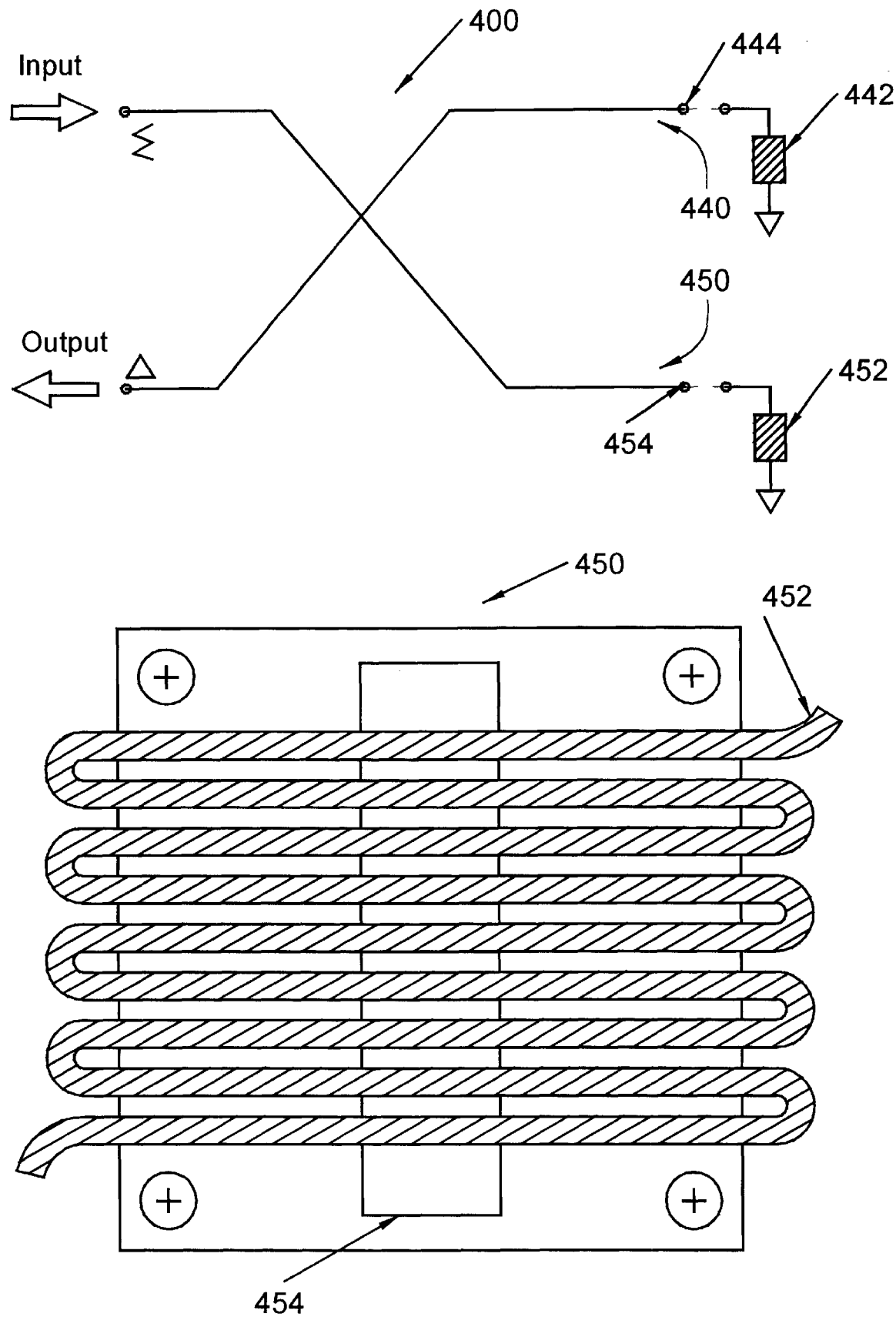
FIG. 4 illustrates a third embodiment of the bioassay device, a waveguide magic-t coupler assembly.

FIG. 4 illustrates a third embodiment of the bioassay device, a waveguide magic-t coupler assembly 400. Known to practitioners in the area of high frequency circuit design, magic-t couplers can be configured to produce an output that represents the difference in the dielectric properties of two loads 442 and 452 connected to the coupler. In the illustrated embodiment, two loads are connected to the magic-t coupler, the first load 442 consisting of a reference sample in which a particular molecular event is known to be present or absent, and the second load 452 consisting of an unknown sample that is being interrogated for the presence of the particular molecular event. A test signal at one or more frequencies is propagated into the $\Sigma$ (sum) port and is electromagnetically coupled to the loads. The resulting output signal at the $\Delta$ (delta) port represents a comparison between the dielectric properties of the two loads 442 and 452.

The waveguide magic-t coupler includes two load ports 444 and 454 consisting of waveguide apertures over which the load 452, consisting of a section of meandered tubing (PTFE in one embodiment) is positioned. Tubing 452 is operable to transport the sample to, and contain it within, a cross sectional area across the waveguide aperture 454 where the incident test signal electromagnetically couples to the sample. In a specific embodiment, the magic-t assembly consists of an X-band magic-t coupler (available from Penn Engineering North Hollywood, Calif.) and 0.020" ID PTFE tubing.

Sample Handling

Figure 5:
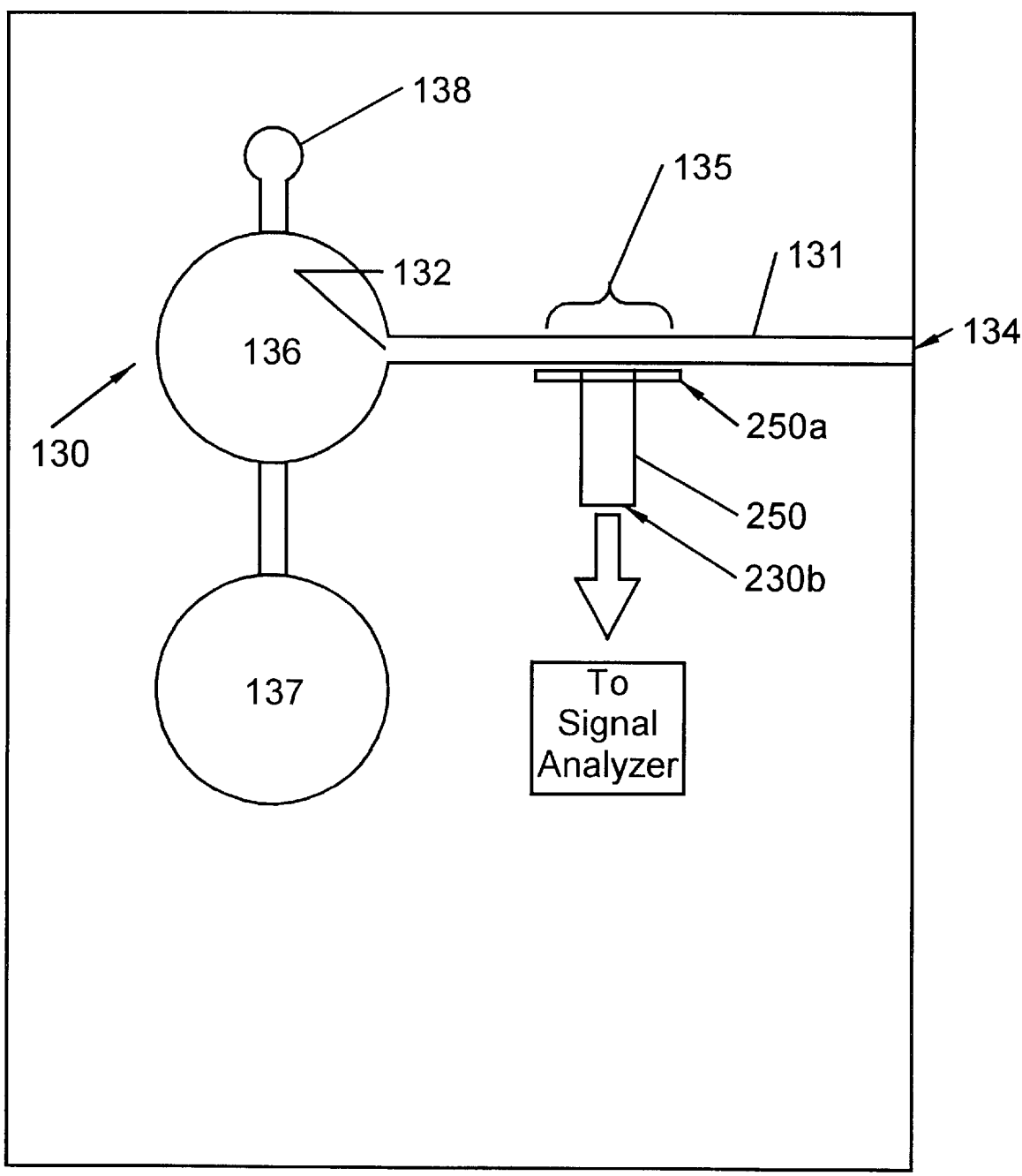
FIG. 5 illustrates an embodiment of a coaxial probe integrated with a fluidic transport system in accordance with the present invention.

FIG. 5 illustrates an embodiment of a coaxial probe 250 (FIG. 2) integrated with a fluidic transport system 130 in accordance with one embodiment of the present invention. The fluid transport system 130 includes a fluid channel 131 through which the test sample flows. Depending upon the application, the fluid channel 131 can take on a variety of forms. For instance in one embodiment, the fluid channel 131 is a Teflon® (polytetrafluoroethylene; PTFE) or other hard plastic or polymer tube (for example TEZEL™ (ETFE) tube) operable to transport the test sample to and from the detection region 131. In another embodiment, the channel 131 consists of one or more etched channels (open or enclosed) in a microfluidic transport system, further described below. Two or more channels can be used to provide a larger detection region 135 to improve detection sensitivity. In another embodiment, the fluid channel 131 is formed through well-known semiconductor processing techniques. Those of skill in the art will appreciate that other construction and architectures of the fluid channel 131 can be adapted to operate under the present invention.

The buffer can consist of a variety of solutions, gases, or other mediums depending upon the particular analyte therein. For example, when the detection system of the present invention is used to detect the presence and/or binding of biological analytes, Dulbecco's phosphate buffer saline (d-PBS) or a similar medium can be used as a buffer to provide an environment which resembles the biological molecule's natural environment. As appreciable to those skilled in the art, other buffers such as DMSO, sodium phosphate (Na3PO4), MOPS, phosphate, citrate, glycine, Tris, autate, borate as well as others can be used in other embodiments under the present invention.

The fluid channel 131 includes a detection region 135 over which the coaxial probe 250 illuminates the sample.

Molecular event detection and/or identification can be accomplished in "solution phase" where the molecular events are free-flowing in the test sample as they move through the detection region, or alternatively in "solid phase," in which probes are deposited or otherwise formed over the detection region and targeted molecular events attach thereto. The area of the detection region 135 will be influenced by several factors including the architecture and material composition of the fluid channel 131, concentration of the molecular events occurring within the solution, desired detection time, the rate at which the test sample advances through the channel, and other factors as appreciable to those skilled in the art. In those embodiments in which detection occurs using immobilized probes, probes are formed within the detection region 135, the area of which will be influenced by binding surface chemistry, the material and morphology of the binding surface, and other factors appreciable to those skilled in the art. Exemplary dimensions of the binding surface will be on the orders of $10^{-1}$ m$^2$ to $10^{-15}$ m$^2$ or any range within these limits. The larger numbers in this range are preferably achieved in a small volume by using a convoluted or porous surface. Smaller numbers within those listed will be more typical of microfluidic devices and systems fabricated using semiconductor processing technology. The detection region 135 can alternatively be modified to accommodate other diagnostic applications, such as proteomics chips, known in the art. The size or shape of detection region need only be such that signal propagation thereto and analyte passage therethrough are possible, subject to other constraints described herein.

In the illustrated embodiment of the detector assembly 130, the fluid controller 136 is connected to a reservoir 137. Fluid controller 136 uses fluid from the reservoir 137 to move the test sample through channel 131, which requires less test sample than simple pumping of sample alone through the channel.

A second reservoir 138 can be used to store a second analyte or test sample for mixture in the reservoir 137. In such an embodiment, the fluid controller 136 can be further configured to rapidly mix the two test samples and supply the resulting mixture to the detection region 135. This technique (known as stopped-flow kinetics in the art of fluidic movement systems) permits the operator to observe and record changes in the signal response as binding events occur between analytes of the two test samples. This data can also be used to determine the kinetics of binding events occurring between the analytes of the two samples. The fluidics of conventional stopped-flow kinetic systems, such as model no. Cary 50 available from Varian Australia Pty Ltd. of Victoria, Australia, can be adapted to operate with the present invention or integrated within the detector assembly 130. See www.hitechsci.co.uk/scientific/index.html for additional information about stopped-flow fluidic systems.

Other components can be included to regulate the test sample flow through the channel 131. The fluid controller 136, fluid reservoirs 137 and 138 and other components associated with fluidic movement can comprise discrete components of the fluid transport system 130 or alternatively be partially or completely integrated.

Figure 6:
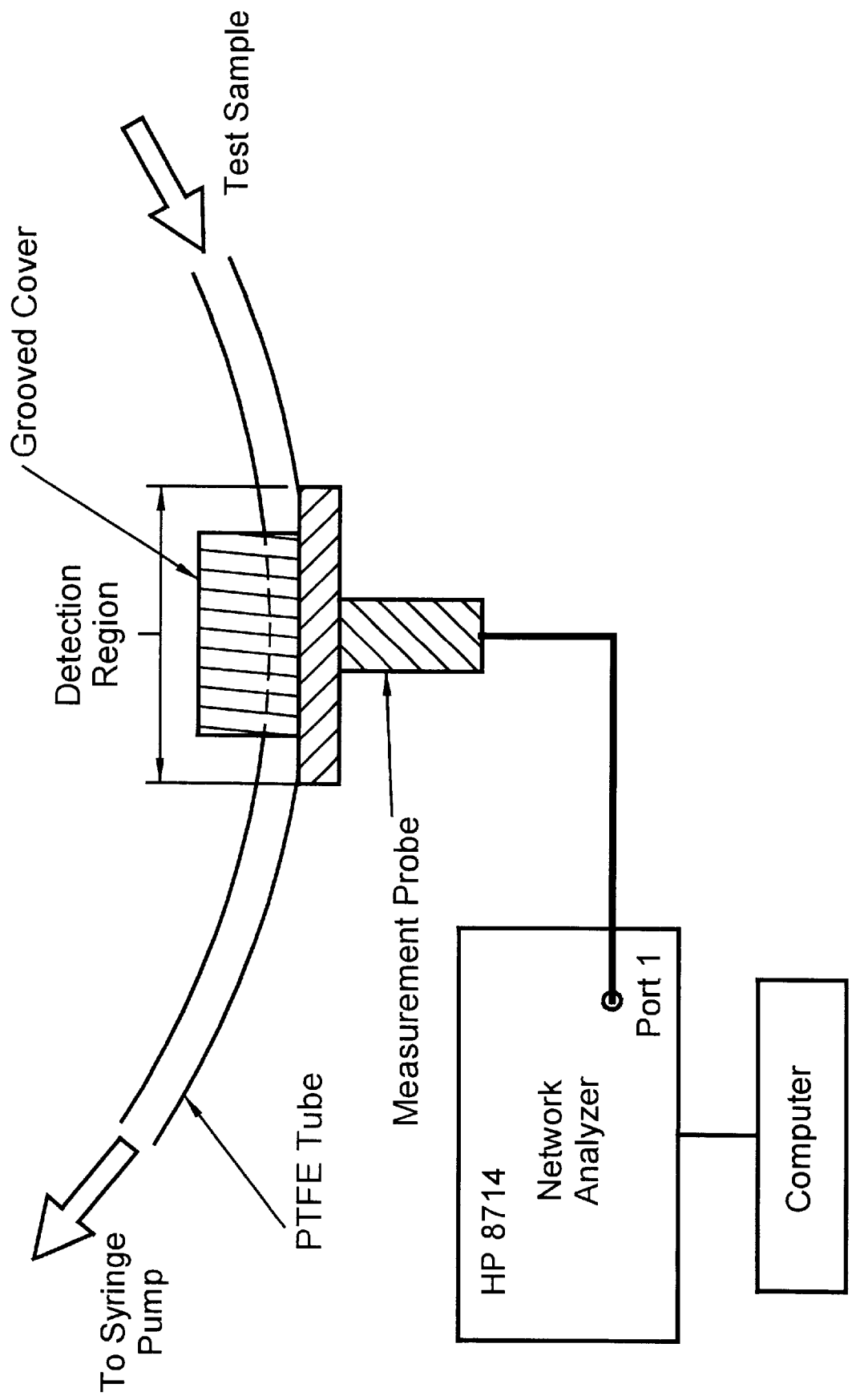
FIG. 6 illustrates a bioassay test system in which a flow tube is used to supply the sample to a coaxial probe in accordance with the present invention.

FIG. 6 illustrates a bioassay test system in which a flow tube is used to supply the sample to a coaxial probe in accordance with the present invention. The system includes a vector network analyzer model number HP 8714 available from Agilent Technologies, Inc. (formerly the Hewlett Packard Corporation), a computer, an open-ended coaxial measurement probe functioning as the bioassay device, and a length of PTFE tube (Cole-Parmer Instrument Company of Vernon Hills, Ill.) used as a fluid channel to transport the transporting medium and test sample to the detection region of the measurement probe. The PTFE tube (0.031" I.D., 0.063" O.D., wall 0.016") is located over the detection region of the measurement probe and is secured using a grooved top cover that was screwed into the shelf of the measurement probe. The tubing extends from the measurement probe in two directions. One end of the tubing is connected to a syringe pump while the other end was immersed in the fluidic test sample to be analyzed. The syringe pump provided negative pressure that was applied to pull the test sample through the tube and over the detection region. In a specific embodiment, the syringe pump aspirates fluid at a rate of ~0.05 mL/min. Further preferred is the introduction of air gaps between two test samples to prevent mixing.

Figure 7:
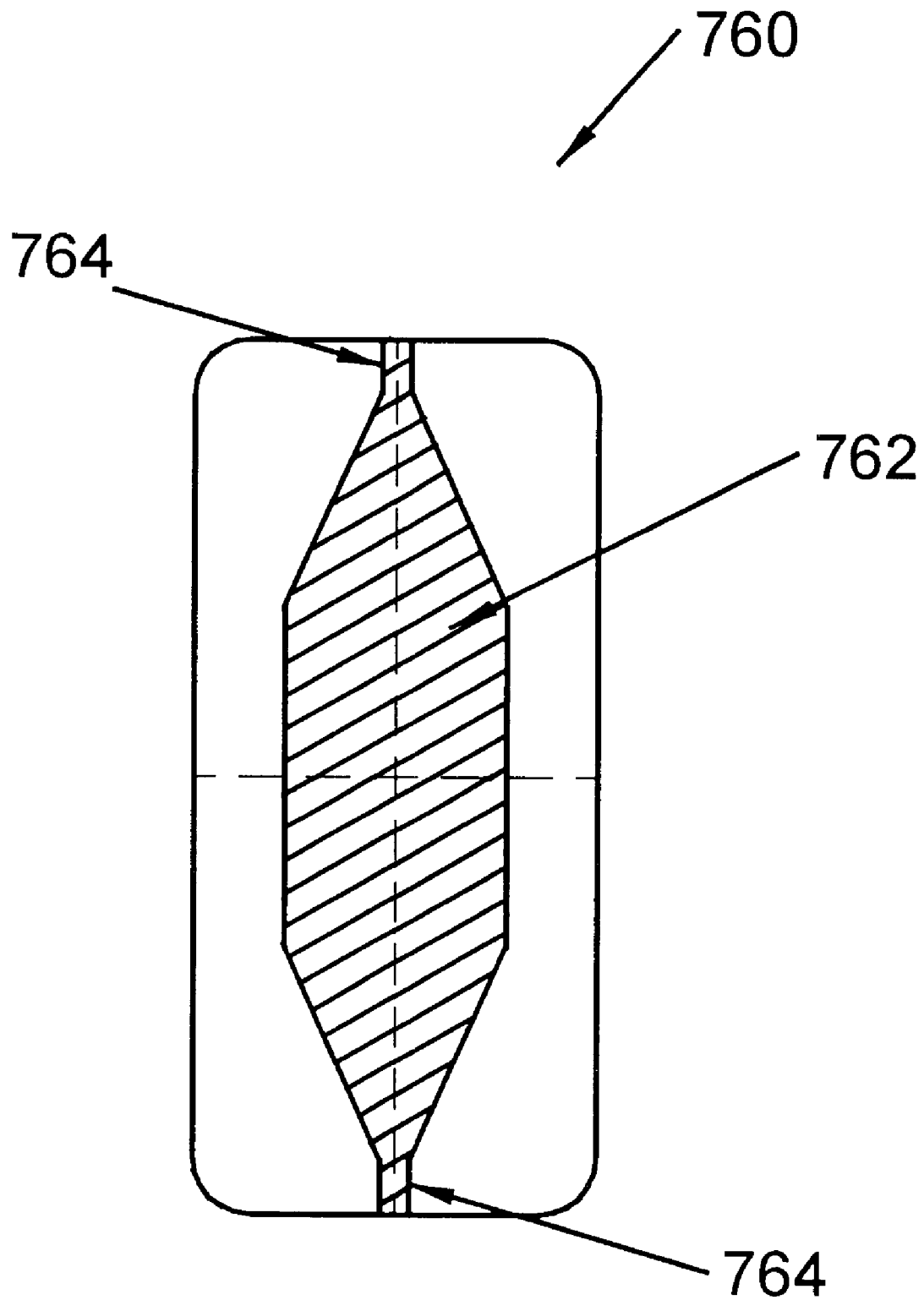
FIG. 7 illustrates a flow cell for use with the waveguide magic-t detector shown in FIG. 4 in accordance with the present invention.

FIG. 7 illustrates a flow cell 760 for use with the waveguide magic-t detector shown in FIG. 4. The flow cell 760 is sized to fit into the waveguide aperture 754 located at the load ports and is constructed from acrylic ([poly] methylmethacrylate) in one embodiment. The flow cell 760 includes a sample chamber 762 (holding 25 μl in one embodiment) and inlet/outlet needles 764, which are UV epoxied to the ends of the chamber 762. Preferably, the diameter of needles 764 is chosen to insert securely within a section of tubing (0.020" ID PTFE tube in one embodiment) which supplies the sample.

IV. Exemplary Temperature Control System

Figure 8:
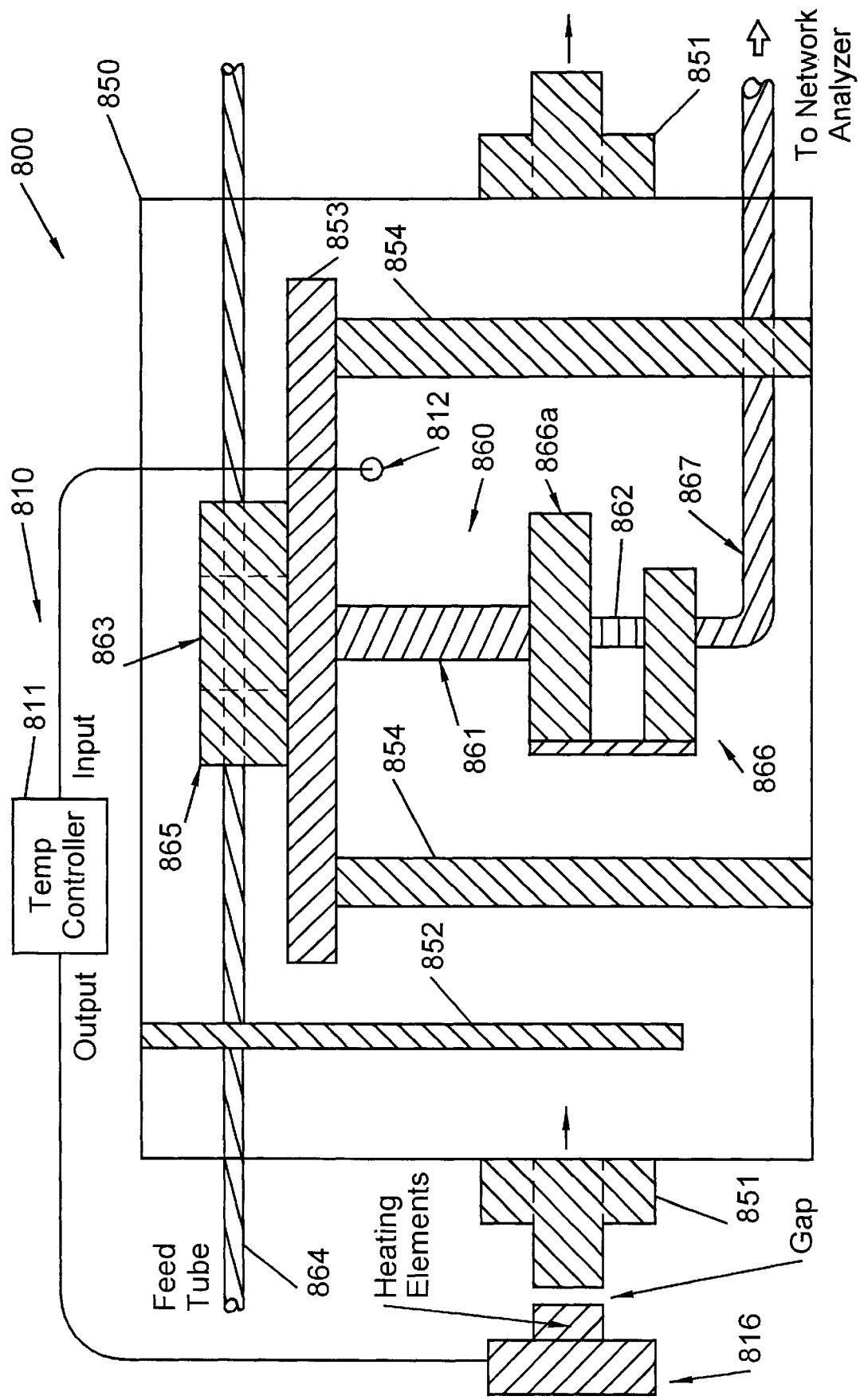
FIG. 8 illustrates a temperature controlled bioassay test set in accordance with one embodiment of the invention.

FIG. 8 illustrates a temperature controlled bioassay test set 800 in accordance with one embodiment of the invention. The set-up 800 includes a temperature control system 810, a temperature-controlled chamber 850, and a bioassay assembly 860.

The temperature control system 810 includes a temperature controller 811, a Resistance Temperature Detector (RTD) 812, and a fan and heating assembly 816. The temperature controller 811 includes a panel for entering in a desired RTD temperature and a readout displaying the current RTD temperature. The RTD 812 is connected to the input port of the controller 811 and is located inside the chamber 850 to monitor the interior temperature. The fan and heating assembly 816 is connected to the controller's output port and used to heat or cool the chamber 850 responsive to the desired input temperature. In a specific embodiment, the temperature controller 811 is model no. CN76000 (Omega Engineering, Inc., Stamford, Conn.) and the heating and cooling assembly 816 is model no. 18TP-1-10 (Payne Engineering, Scott Depot, W. Va.)

The temperature-controlled chamber 850 includes air intake/exhaust nozzles 851, an airflow diverter 852, support shelf 853 and support posts 854. The air intake nozzle 851 is physically separated from the fan and heating assembly 816 by a gap in order to provide the chamber 850 mechanical isolation from vibrations created by the fan and heating assembly 816. The airflow diverter 852 functions to redirect and circulate the incoming airflow through the chamber 850. A support shelf 853 configured to support the bioassay assembly 860 is elevated by support posts 854. In one embodiment, the outer walls of the chamber 850, air nozzles 851, flow diverter 852, and support posts 854 are constructed from Acrylic and the chamber measures approximate 10" deep, 11.5" high and 7" wide. The support shelf is fabricated from aluminum in one embodiment.

The bioassay assembly, an open-ended coaxial resonator in the illustrated embodiment, includes a first coaxial section 861, a second coaxial section 862, a flow cell 863, feed tube sections 864, a cap plate 865, a tuning assembly 866, and a coaxial cable 867. The first coaxial section 861 includes an open-ended cross section over which a flow cell 863 is positioned. The flow cell 863 is preferably constructed from a material that is substantially transparent (i.e. has low signal loss) to the applied test signal. Feed tubes 864 (PTFE in one embodiment) are connected to the flow cell 863 and configured supply the sample thereto. The cap plate 865 serves to retain the flow tube sections 864 connected to the flow cell 863 and to align the flow cell 863 over the open-ended portion of the first coaxial section 861. In one embodiment, the cap plate 865 may include a center bore for accepting a small container such as an open well. The length of the first coaxial section 861 is selected to be approximately one-half of one wavelength ($\lambda/2$) long at the desired resonant frequency.

The tuning assembly 866 includes a bracket 866a which has a hollow gap region formed between the first and second coaxial sections 861 and 862. The tuning assembly 866 is operable to adjustably move the second coaxial section 862 into and out of the hollow region within bracket 866a. The second coaxial section 862 is connected to the coaxial cable 867, which is in turn connected to the measurement system, a network analyzer in one embodiment of the present invention.

V. Exemplary Methods and Application

The apparatuses and sub-assemblies described herein can used to provide information about numerous properties of a test sample, such as the detection and identification of molecular binding events, analyte concentrations, changes in dielectric properties of the bulk test sample, classification of detected binding events, and the like. Preferred methods involve detection of molecular events, and the precise temperature controls described here greatly improve the reliability of such measurements. However, an apparatus of the invention can be used for other purposes as well, as the accuracy of permittivity measurements is increased by the methods and apparatuses described herein, regardless of their intended use. Based upon the described methods and structures, modifications and additional uses will be apparent to those skilled in the art.

The herein-described systems and methods can be used in a variety of analytical applications. In one embodiment, the present invention can be used in methods that identify substructures or binding events involving analytes, for example proteins. In a calibration phase of such analyses, the signal responses of a large number of known proteins can be determined and stored. After introducing an unknown protein to the detection region, the dielectric properties of the system can be measured and the dielectric properties of the signal used to identify the protein's properties. Because each protein's fingerprint response is stored, the unknown response can be compared with the stored responses and pattern recognition can be used to identify the unknown protein.

In another embodiment, the invention can be used in a parallel assay format. The device in such a format will have multiple addressable channels, each of which can be interrogated separately. After delivering a test sample or samples to the device, responses at each site will be measured and characterized. As an example, a device of this type can be used to measure and/or identify the presence of specific nucleic acid sequences in a test sample by attaching a unique nucleic sequence as the antiligand to the detection region or a part thereof. Upon exposure to the test sample, complementary sequences will bind to appropriate sites. The response at each site will indicate whether a sequence has bound. Such measurement will also indicate whether the bound sequence is a perfect match with the antiligand sequence or if there are one or multiple mismatches. See, for example, U.S. application Ser. No. 09/365,581 (from the laboratories of the present inventors), which describes this method in detail. This embodiment can also be used to identify proteins and classes of proteins, by analyzing signals obtained from a particular sample and comparing that signal to signals obtained from a collection of known proteins.

In another embodiment, the present invention can be used as part of a technique that generates a standard curve or titration curve that would be used subsequently to determine the unknown concentration of a particular analyte or ligand binding curve. For example, an antibody could be attached to the detection region. The device could be exposed to several different concentrations of the analyte and the response for each concentration measured. Such a curve is also known to those skilled in the art as a dose-response curve. An unknown test sample can be exposed to the device and the response measured. Its response can be compared with the standard curve to determine the concentration of the analyte in the unknown test sample. Similarly, binding curves of different ligands can be compared to determine which of several different ligands has the highest (or lowest) affinity constant for binding to a particular protein or other molecule.

In another embodiment, this invention can be used with embodiments that calibrate for losses due to aging and other stability issues. For example with antibody-antigen systems, one can measure the amount of active antibody in a test sample. The signal response is compared to standard signals for samples of known activity in order to determine the activity of the unknown.

Detecting Molecular Events

The present invention enables the detection of the presence of a molecular structure or of molecular binding events in the detection region of the detection system. Detectable binding events include primary, secondary, and higher-order binding events. For instance, mixing of two test solutions can lead to binding between ligand/antiligand pairs, or to simple mixing without binding if the two components have no affinity for each other. For example, a solution is provided which contains a test molecule or molecular structure. A test signal is propagated along the signal path and coupled to the sample. Alternatively, the test signal can be launched during or shortly after a mixing operation in order to observe in real time the signal response occurring as a result of binding events. The test signal is recovered, the response of which indicates detection of the analyte, substructure, or binding event.

The dielectric property of a test sample induce numerous signal responses, each of which can be indicative of molecular binding (with appropriate signal analysis). For instance, the dispersive properties of the test sample can vary dramatically over frequency. In this instance, the test signal response will exhibit large changes in the amplitude and/or phase response over frequency when molecular events occur in the detection region, thereby providing a means for detecting molecular binding events or other time dependent events after the mixing of test samples.

In another embodiment, the dielectric relaxation properties of the test sample in the detection region will vary as a function of pulse period of the input signal. In this instance, the test signal response will indicate a change in the amount of power absorbed, or change in some other parameter of the test signal like phase or amplitude, at or near a particular pulse period. By observing a change in the absorbed power or other parameters, binding events can be detected. Other quantities such characteristic impedances, propagation speed, amplitude, phase, dispersion, loss, permittivity, susceptibility, frequency, and dielectric constant are also possible indicators of molecular presence or binding events. Important information regarding molecular properties can also be determined by measuring signals, such as these, during changes in the environment of the molecular structure being detected (such as changes in pH or ionic strength).

The above-described method can be used to detect the primary binding of an antiligand and ligand. Similarly, the process can also be used to detect secondary binding of a ligand to an antiligand. The method not limited to detection of primary or secondary binding events occurring along the signal path. Indeed, tertiary, and higher-order binding events occurring either along the signal path or suspended in solution can be detected using this method.

For example, initially a primary binding event is detected and the signal response measured, as described herein. Subsequently, the primary binding event signal response is stored and used as a baseline response. Next, a second molecular solution is added to the assay device. Detection steps are repeated to obtain a second signal response. Next, the second signal response and the baseline response are compared. Little or no change indicates that the two signal responses are very close, indicating that the structural and dielectric properties of the test sample have not been altered by the addition of the molecules within the new solution. In this case, secondary binding has not occurred to a significant degree. If the comparison results in a change outside of a predetermined range, the structure and/or dielectric properties of the test sample have been altered, thereby indicating secondary binding events. Quantities which can be used to indicate secondary binding events will parallel the aforementioned quantities, e.g., amplitude, phase, frequency, dispersion, loss, permittivity, susceptibility, impedance, propagation speed, dielectric constant as well as other factors. Tertiary or high-order binding events can be detected using this approach.

An alternative method of detecting secondary or higher order binding events does not required prior knowledge of the specific primary binding event. In this embodiment, the assay device is designed in the assay development stage to operate with known parameters, so that whenever a predefined change in one of these parameters is detected, for example at the point-of-use, the binding event or events are then known to have occurred. In this embodiment, the pre-measurement of a primary binding event is not necessary, as the initial characterization has already been done either at the time of fabrication or at the time of design.

Secondary binding events can also be achieved by detecting changes in the structure of the primary molecules structure. When a molecule becomes bound, it undergoes conformational and other changes in its molecular structure relative to its unbound state. These changes affect the primary binding molecule's dielectric properties as well as inducing changes in the surrounding solution, the variation of which can be detected as described above. Quantities that can be monitored to indicate a change in the dielectric properties of the primary bound molecule include the aforementioned quantities, e.g., amplitude, phase, frequency, dispersion, loss, permittivity, susceptibility, impedance, propagation speed, and dielectric constant, as well as other factors.

Detecting Changes in the Dielectric Properties of the Test Sample

The detection systems described herein can also be used to measure the dielectric changes of the test sample as a result changes in temperature, pH, ionic strength and the like. The process closely parallels the disclosed method for identifying binding events, the exception being that the method allows for the detection and quantitation of changes in dielectric properties of the test sample without reference to a binding event.

The process begins when a solution having an initial dielectric property is added to the detector assembly. The signal response is measured and recorded, as previously described. After a predetermined time or operation, a second measurement is made and a second signal response is recorded. A comparison is then made between the first and second signals to determine whether the two signals correlate within a predefined range. If so, the properties of the solution are deemed to not have undergone any dielectric changes.

If the signal responses do not correlate within a predefined range, at least dielectric property of the solution will have undergone a change. Optionally, the change in dielectric properties can be quantitated. For example, the second signal is stored and correlated to a known signal response. The closest correlated response will identify the dielectric property of the solution and the first signal response can be correlated to the initial value of the dielectric property, the difference of which can be used to determine the amount by which the identified dielectric property has been altered.

Identifying Molecular Structures

Using the described detector assemblies, it is possible to characterize a known analyte and subsequently identify it in a solution having an unknown analyte make-up. For example, a large number of molecular structures and/or substructures are measured and their responses stored using one or more of the measurement systems, described below. Each stored response will correspond to a single structure/substructure occurring within the solution or multiple structures/substructures occurring within the same solution. Subsequently, a measurement is made of an unknown solution. Next, the signal response of the solution is compared to the stored signal responses to determine the degree of correlation therewith. The unknown molecular structure is identified by selecting the stored response that exhibits the closest correlation to the unknown response. The comparison can be performed using one or more data points to determine the correlation between one or more stored responses, and can involve the use of pattern recognition software or similar means to determine the correlation. The process can be used to identify an individual structure/substructure, as well as primary, secondary or higher-order bound molecular structures.

Identifying Classes of Molecular Structures

It is also possible to characterize known molecular substructures such as domains or other structural homologies that are common to similar classes of proteins or sequence homologies in nucleic acids. In one embodiment, the process proceeds as shown in section D immediately above, except that a number of molecular sub-structures are measured and their responses stored. Each stored signal response will correspond to one or more sub-structures. The process continues until a sufficient number or structures have been detected and characterized to identify the unknown compound. Once a sufficient number of correlations occur, it is then possible to classify the unknown molecular structure.

There are other processes by which unknown analytes can be classified. One process identifies the unknown analyte by detecting binding to structural motifs on the unknown compound. Initially, a detector assembly can be provided which has multiple addressable parallel channels, each of which has a antiligand for a specific ligand sub-structure bound in the detection region. Next, the presence of particular sub-structures is detected by the binding of each to its respective antiligand and subsequent characterization. In one embodiment, this step is performed as described above, but other variations can be carried out as well. Subsequently, each of the binding events is then characterized by identification of qualities such as affinity, kinetics, and spectral response. A correlation is then made between the known and unknown responses. If each of the unknown responses correlates to known responses, the ligand is identified as the ligand corresponding to the known response. If the substructures exhibit both correlated and uncorrelated responses, the correlated responses can be used to construct a more general classification of the unknown ligand. This process can be used to identify any molecular structure, for example proteins, which occur within the same class or have re-occurring structural homologies.

It is also possible that an intensive spectral analysis of a given unknown compound could lead to insights on structure and function, as comparisons can be made to known structures, and extrapolation will lead to some level of classification.

Specific vs. Non-Specific Binding

Specific binding can be distinguished from non-specific binding by the spectral fingerprint of the binding events. Indeed, any two binding events, such as the binding of one molecular structure on separate occasions with two similar but different molecular partners, can generally be distinguished by the spectral fingerprints of the two binding events. For example, a given binding event of interest, such as antibody binding to antigen, can be first characterized in a purified solution containing just the ligand of interest and the antiligand specific to the ligand. A broad spectral study is then carried out to see when in the spectrum the strongest responses are found. The assay is then repeated in the solutions typically found in the dedicated applications, for example whole blood, to determine what effects non-specific binding has on the response. Then various points are found which are determinate of specific binding, and a separate set of points are found which are determinate of non-specific binding, and a subset of these frequency points are chosen for the actual assay application. By comparing the response due to specific binding with those due to the non-specific binding, the extent of specific binding can be determined.

Characterization of a Given Analyte

Often it is desirable to determine certain qualities of a given molecule. Examples in include determining the class to which a protein belongs, or which type of polymorphism a given gene or other nucleic acid sequence is. This can be done in a number of ways. Proteins are often classified by number and types of structural homologies, or particular substructures which are found in the same or similar classes of proteins. For example, G-Proteins commonly found in cell membranes and which mediate signal transduction pathways between the extracellular environment and the intra-cellular environment, always have a structure which traverses the cell membrane seven times. Such a structure is virtually definitive of a G-Protein. Other classes of proteins have similar structural homologies, and as such, any method which can distinguish one class of proteins from another on the bases of these homologies is of enormous use in many of the biomedical research fields. Given that the dielectric properties of a given molecule is determined by the geometry of the charge distribution of the molecule, and further given that most proteins have a unique structure or geometry, then each protein can be uniquely determined by measuring the dielectric properties of the protein. Thus a simple dielectric signature, such as the ones generated by the present invention, can serve to uniquely identify a given protein, and further, can allow classification of the protein into some previously known class of proteins. A further refinement can be added to the classification methodology by using a group of anti-ligands on the detector assembly which are specific for particular sub-structures of a given protein. For example, a group of antibodies that are specific for particular sub-structures, such as domains, can be utilized for the determination of the existence or absence of the substructures. Thus, any given protein can be characterized by determining both the presence and absence of certain sub-structures as well as the dielectric properties of the protein itself. Further refinements to this classification strategy can include looking at temperature, pH, ionic strength, as well as other environmental effects on the above-mentioned properties.

Nucleic acids can also be characterized by following a similar paradigm. For example, a given gene can be known to have a certain base pair sequence. Often times in nature there will be small variations in this sequence. For example, in the gene which codes for a chloride ion transport channel in many cell membranes there are common single base-pair mutations, or changes. Such changes lead to a disease called cystic fibrosis in humans. Thus characterizing a given nucleic acid sequence with respect to small variations is of enormous importance. Such variations are often called polymorphisms, and such polymorphisms are currently detected by forming complementary strands for each of the known polymorphisms. Since any given gene can take the form of any one of hundreds or even thousands of polymorphisms, it is often an arduous task to generate complementary strands for each polymorphism. Using the invention described herein, non-complementary binding or hybridization can be detected and distinguished by measuring many of the same physical properties as were described in the previous paragraph: The dielectric properties of the hybridization event can be characterized and correlated to known data, thereby determining the type of hybridization which has occurred—either complete or incomplete. Thus with an antiligand comprised of a given nucleic acid sequence, hundreds of different polymorphisms (as ligands) can be detected by the characterization of the binding event. One of skill in the art will appreciate that further refinements are possible, such as modifying the stringency conditions to alter the hybridization process, or varying the temperature and determining the melting point, which serves as another indicator of the nature of the hybridization process.

In a similar manner, drug-receptor interactions can be characterized to determine is a given binding event results in the receptor being turned on or off, or some other form of allosteric effect. For example, a given receptor can be used as an antiligand, and a known agonist can be used as the first ligand. The interaction is then characterized according to the dielectric response, and this response is saved. Subsequently, compounds that are being screened for drug candidates are then observed with respect to their binding properties with the receptor. A molecule that binds and yields a similar dielectric response is then known to have a similar effect on the receptor as the known agonist, and therefore will have a much higher probability of being an agonist. This paradigm can be used to characterize virtually any type of target-receptor binding event of interest, and represents a significant improvement over current detection strategies which determine only if a binding event has occurred or not. Those of skill in the art will readily appreciate that there are many other classes of binding events in which the present invention can be applied.

Examples of sub-structures which can be used in the above method include: Protein secondary and tertiary structures, such as alpha-helices, beta-sheets, triple helices, domains, barrel structures, beta-turns, and various symmetry groups found in quaternary structures such as $C_2$ symmetry, $C_3$ symmetry, $C_4$ symmetry, $D_2$ symmetry, cubic symmetry, and icosahedral symmetry. [G. Rose (1979), Heirarchic Organization of Domains in Globular Proteins, *J. Mol. Biol.* 134: 447–470] Sub-structures of nucleic acids which can be analyzed include: sequence homologies and sequence polymorphisms, A, B and Z forms of DNA, single and double strand forms, supercoiling forms, anticodon loops, D loops, and TψC loops in tRNA, as well as different classes of tRNA molecules. [W. Saenger (1984) *Principles of Nucleic Acid Structure.* Springer-Verlag, New York; and P. Schimmel, D. Soll, and J. Abelson (eds.) (1979) *Transfer RNA.* Cold Spring Harbor Laboratory Press, Cold Spring Harbor, N.Y.]

Quantitating Concentrations

The detector assemblies described herein can also be used to quantitate the concentrations of analytes. In one such one embodiment of this process, in which the device is not pre-calibrated, initially anti-ligands are chosen having the appropriate binding properties, such as binding affinity or kinetics, for the measured analyte. These properties are selected such that the anti-ligand's equilibrium constant is near the center of its linear operating region. For applications where the range of concentration is too wide for the use of a single antiligand, several anti-ligands can be used with differing affinities and/or linear operating ranges, thereby yielding a value for the concentration over a much wider range.

Next, the anti-ligands are added or attached to the detector assembly or chip and the device is connected to the measurement system. A decision is then made as to whether the response requires characterization for maximum specificity. If so, a spectral analysis is performed in which the frequency or frequencies where analyte binding has maximal effect on the signal are determined, the regions where the non-specific binding has maximal effect are determined, and the response due to analyte binding is determined. If characterization is not required, or if so, after its completion, the device is calibrated. This step is performed in one embodiment by supplying a known concentration of ligands to the detector assembly and measuring the resulting response. Alternatively, if more data points are needed for the calibration, then a test sample can be chosen with a different concentration, and the response against this concentration can be measured. Subsequently, an extrapolation algorithm is generated by recording the calibration points from the foregoing response. Next, a test sample of unknown analyte concentration is measured. This step is accomplished in one embodiment by supplying the unknown test sample to the detector assembly, correlating the response to the titration algorithm, and determining therefrom the analyte concentration.

In the event that a given detector assembly is either precalibrated, or calibrated by design, the only step required is to mix the binding pairs and measure the response. Such a detector assembly can be realized in many different ways. For example, some circuit parameter, such as impedance or characteristic frequency of a resonant circuit, can be designed to change in a pre-determined way when the binding event occurs, and the amount by which the parameter changes can further be designed to have a dose-response. Thus, a measurement of the circuit parameter will, when analyzed via a suitable algorithm, immediately yield a quantitative value for the concentration of a given analyte or ligand.

Detector Assembly Self-Calibration

The detector assembly possess a self-diagnostic capability and thus a point-of-use quality control and assurance. For a given dedication application, a particular antiligand primary binding species) will act as an antiligand for some ligand (the secondarily binding species) of interest in the solution. The primary binding species can be attached at the point of fabrication, and the secondary binding species can be attached at the point-of-use. Thus, variations in fabrication—specially the attachment of the primary species—will cause variations in the ability of the device to bind its specific ligand. However, the amount of ligand bound will be in direct proportion to the amount of antiligand bound, thus a ratiometric measurement of the two is possible.

In one embodiment of the process, a molecular binding surface is formed along the signal path by binding the appropriate antibody at various concentrations and characterizing the resulting response for each of these concentrations, yielding some value "x" for each concentration. Next, a similar titration curve is generated for the ligand by measuring the antibody/ligand binding response for several different concentrations of ligand, and a ligand titration curve is pre-determined. Next, a scale factor A is generated by taking the ratio of responses of antibody binding to ligand binding. At the point-of-use, the uncalibrated assay is then first probed to determine the amount of bound antibody "x" and the scale factor "y" resulting therefrom. The ligand is then applied to the assay and the response is measured, and the response and predetermined titration curve are scaled by the scale factor "y" to determine unknown concentration.

The process can also be modified to allow quantitating the amount of binding in the solution. In the modification, the binding surface of the detector assembly includes antiligands having a predefined affinity and ligand specificity. The solution is subsequently applied to the device, and a response is measured. The signal response will be proportional to the amount of the ligand that has bound. Thus, a titration of any given ligand can be carried out by choosing an antiligand with an appropriate linear operating range—the range in which the equilibrium constant is within a couple of log units of the desired range of concentrations to be detected. The same ratiometric analysis as described above can be applied to yield a robust and precise quantitative assay with internal controls and calibration necessary to insure reliability.

VI. Software Implementation

Each of the measurement and detection methods described herein can be practiced in a multitude of different ways (i.e., software, hardware, or a combination of both) and in a variety of systems. In one embodiment, the described method can be implemented as a software program.

Figure 9A:
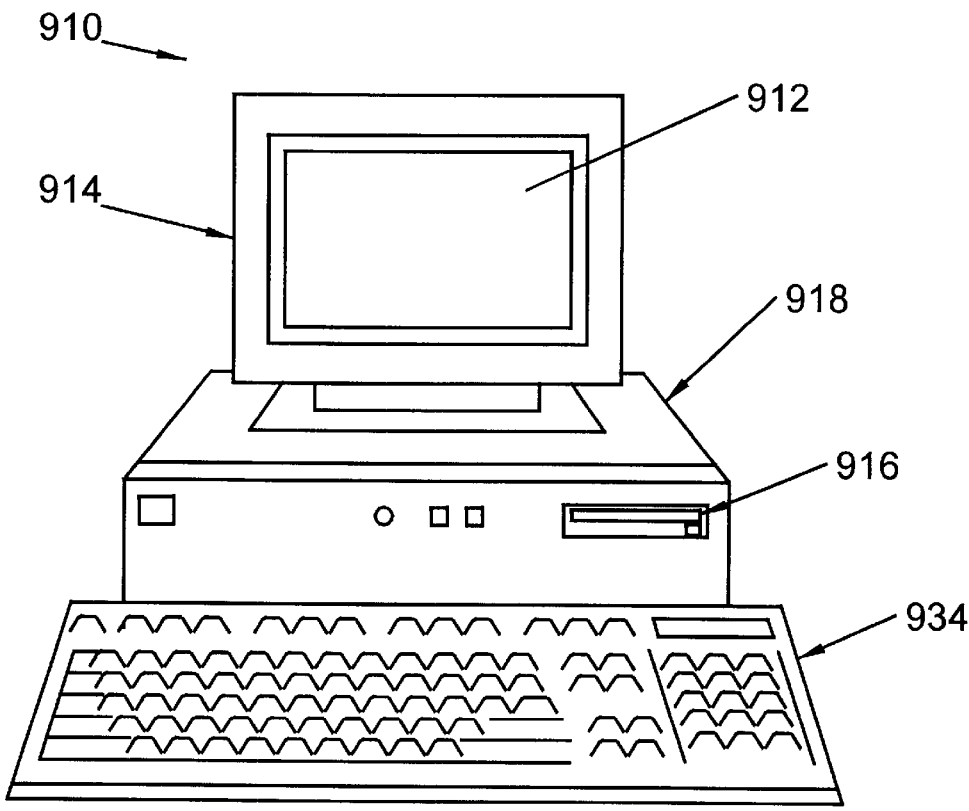
FIG. 9A illustrates a simplified block diagram of a computer system operable to execute a software program designed to perform each of the described methods.

FIG. 9A illustrates a simplified block diagram of a computer system 910 operable to execute a software program designed to perform each of the described methods. The computer system 900 includes a monitor 914, screen 912, cabinet 918, and keyboard 934. A mouse (not shown), light pen, or other I/O interface, such as virtual reality interfaces can also be included for providing I/O commands. Cabinet 918 houses a CD-ROM drive 916, a hard drive (not shown) or other storage data mediums which can be utilized to store and retrieve digital data and software programs incorporating the present method, and the like. Although CD-ROM 916 is shown as the removable media, other removable tangible media including floppy disks, tape, and flash memory can be utilized. Cabinet 918 also houses familiar computer components (not shown) such as a processor, memory, and the like.

Figure 9B:
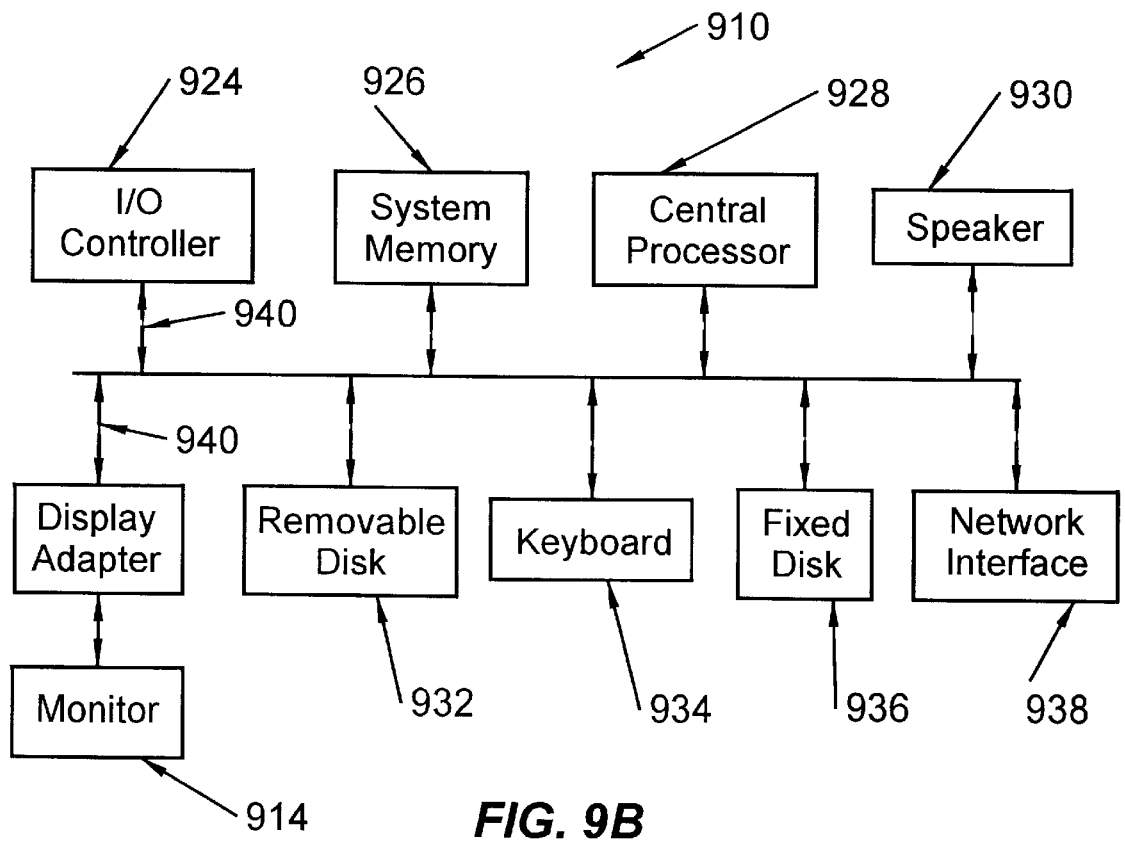
FIG. 9B illustrates the internal architecture of the computer system shown in FIG. 9A.

FIG. 9B illustrates the internal architecture of the computer system 910. The computer system 910 includes monitor 914 which optionally is interactive with the I/O controller 924. Computer system 910 further includes subsystems such as system memory 926, central processor 928, speaker 930, removable disk 932, keyboard 934, fixed disk 936, and network interface 938. Other computer systems suitable for use with the described method can include additional or fewer subsystems. For example, another computer system could include more than one processor 928 (i.e., a multi-processor system) for processing the digital data. Arrows such as 940 represent the system bus architecture of computer system 910. However, these arrows 940 are illustrative of any interconnection scheme serving to link the subsystems. For example, a local bus could be utilized to connect the central processor 928 to the system memory 926. Computer system 910 shown in FIG. 9A is but an example of a computer system suitable for use with the present invention. Other configurations of subsystems suitable for use with the present invention will be readily apparent to of skill in the art.

VII. Experiment

The following example is not an example of a molecular interaction, but nonetheless demonstrates the importance of temperature control by showing how characterization of protein structure (identification of a protein) is affected by temperature changes.

Materials

Bovine serum albumin (BSA) A2153, Human Serum albumin (HSA) A1653, lysozyme from chicken egg white L6876, myoglobin from horse skeletal muscle M0630, ovalbumin A5503, and ribonuclease A (RNase A) from bovine pancreas R5503 were purchased from Sigma (St. Louis, Mo.). The sodium phosphate buffer (25 mM phosphate, 0.05% v/v NP-40 surfactant, pH 7.7) was freshly prepared in 18 mega Ohm water.

Instrumental Setup

The instrumental setup included an Agilent 8714ET RF network analyzer, a Dell personal computer running custom Labview software for recording data, a Newport isolation table with a mounted coaxial resonating detector, a Pico motor from New Focus, a custom fluidic flowcell mounted to the detector (the flowcell is made of poly(etherimide) and has a 0.030 inch internal diameter channel with a thin 0.007 inch bottom) and a temperature controlling apparatus, which housed the detector. The temperature controlling apparatus and the coaxial resonator are described above. Phosphate buffer was loaded into position in the fluidic flowcell by aspiration (150 $\mu$L volume was used) and the resonating detector was tuned to the resonant frequncy point by adjustment of the resonators gap size using the Pico motor. Data was collected at 401 point resolution using a system bandwidth of 15 Hz and a power level of 0 dBm. Two spans 1 MHz and 200 KHz are recorded for purposes of calculating the permitivity of the test samples. The experiment was performed once while using temperature controlling apparatus (with Temperature Control) and a second time after removing the temperature controlling apparatus (without Temperature Control).

The signal for each test sample was recorded 1 minute after it was position in the fluidic flowcell of the apparatus. The 1 minute waiting period was determined to be sufficient to allow for equilibration of the sample to the temperature of the detecting apparatus. The signal was measured for six protein solutions each of which flanked by a measurement of the phosphate buffer, which served as the reference for this experiment. The series of measurements were repeated four times in series. The same buffer and protein solutions were used for the experiment with and without temperature control. Included in each experiment but not shown are the signals for two calibration solutions, which are used for the purpose of calculating the permitivity of the test samples.

Results

Figure 10:
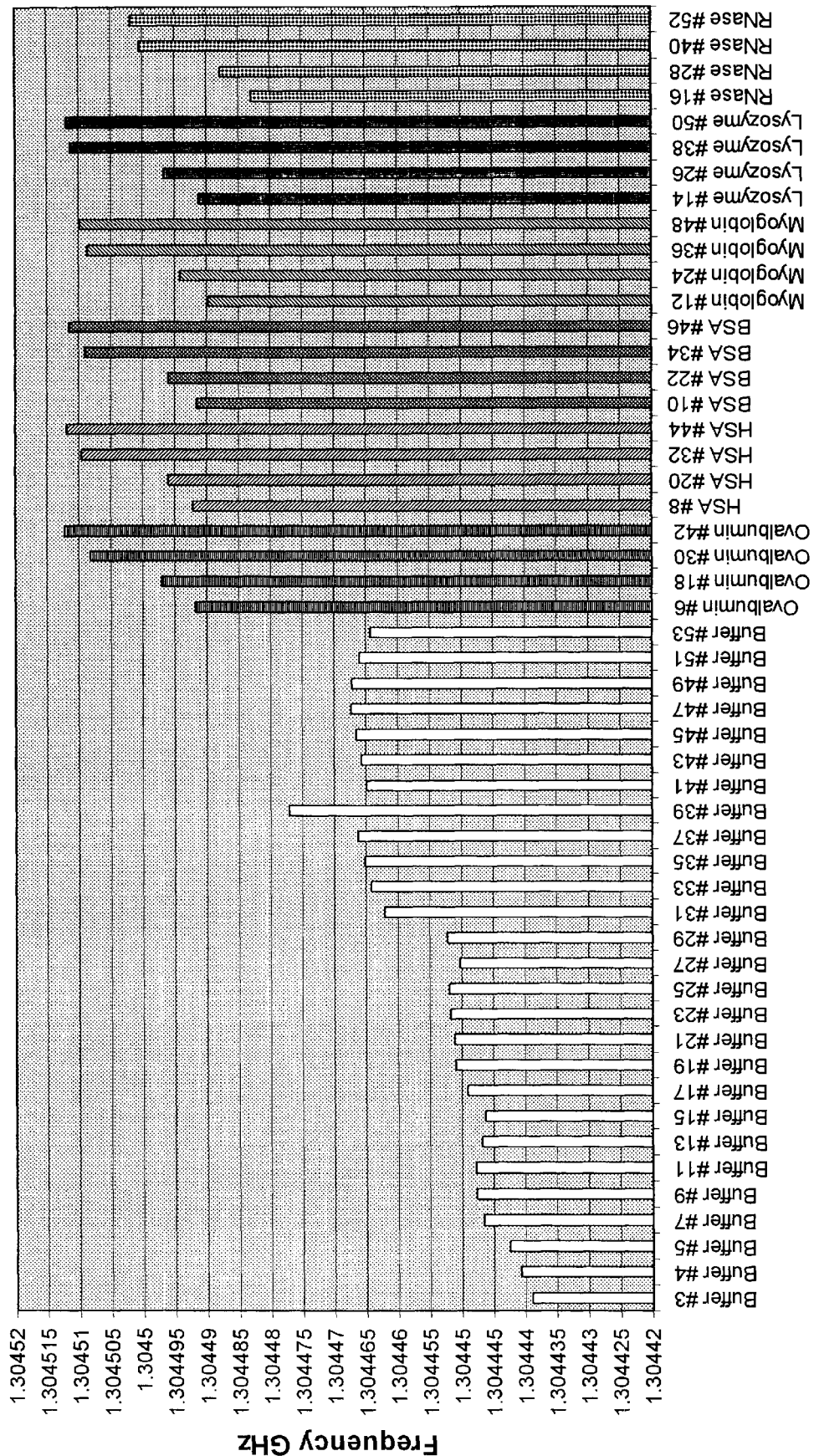
FIG. 10 illustrates an experiment without temperature control.
Figure 11:
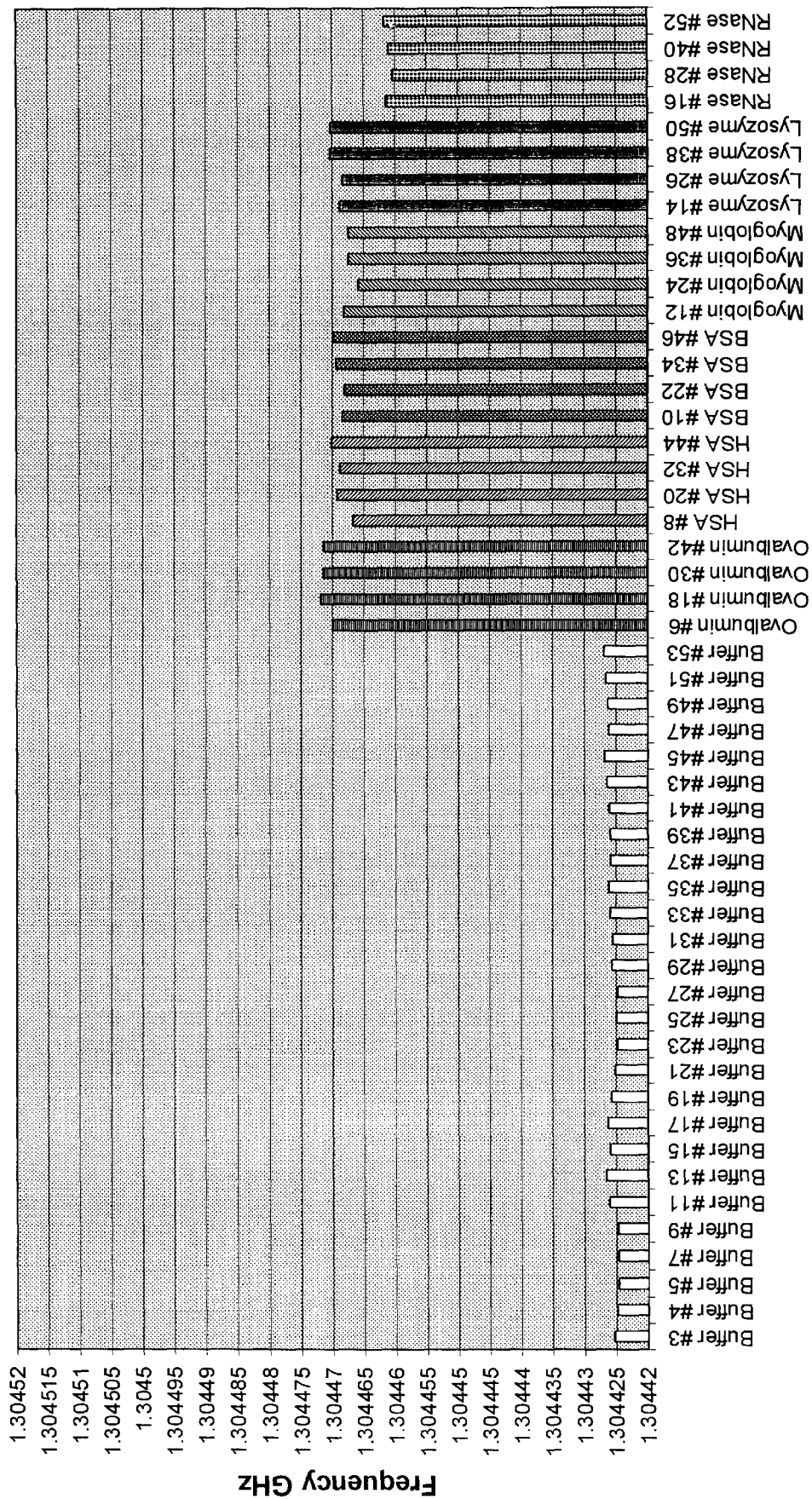
FIG. 11 illustrates an experiment with temperature control.

The center frequency for each measurement was charted using the same y-axis scale for both the experiment without temperature control (FIG. 10) and the experiment with temperature control (FIG. 11). The variance in the centered frequency measured for the buffer measurements (reference signal) is much larger for the experiment without temperature control (38 KHz difference) than that observed for the experiment with temperature (3 KHz difference). The variance in the center frequency for the individual protein solutions is also large for the experiment without temperature control than with temperature control. Each experiment took approximately 2 hours to complete and the temperature measured at the position of the fluidic flowcell for experiment without temperature control ranged from 25.1° C. to 23.2° C.(24.1±1° C.) while the experiment with temperature control ranged from 26.8° C. to 27.2° C. (27.0±0.2° C.). Thus, reducing the temperature variation from ±1° C. to ±0.2° C. by using a temperature controlling apparatus resulted in less variance in the measured frequency values for a series of protein samples.

While the above is a complete description of possible embodiments of the invention, various alternatives, modifications, and equivalents can be used. For example, other transmission mediums, such as conductive or dielectric waveguides, can alternatively be used, as well as other fluid transport systems. Further, all publications and patent documents recited in this application are incorporated by reference in their entirety for all purposes to the same extent as if each individual publication and patent document was so individually denoted. Specifically, this application is related to the following commonly owned, co-pending applications, all of which are herein incorporated by reference in their entirety for all purposes:

Ser. No. 09/243,194 entitled "Method and Apparatus for Detecting Molecular Binding Events, filed Feb. 1, 1999 (Atty Dkt No. 19501-000200US);

Ser. No. 09/243,196 entitled "Method and Apparatus for Detecting Molecular Binding Events," filed Feb. 1, 1999 (Atty Dkt No. 19501-000300US);

Ser. No. 09/365,578 entitled "Method and Apparatus for Detecting Molecular Binding Events," filed Aug. 2, 1999 (Atty Dkt No. 19501-000210);

Ser. No. 09/365,978 entitled "Test Systems and Sensors for Detecting Molecular Binding Events," filed Aug. 2, 1999 (Atty Dkt No. 19501-000500);

Ser. No. 09/365,581 entitled "Methods of Nucleic Acid Analysis," filed Aug. 2, 1999 (Atty Dkt No. 19501-000600);

Ser. No. 09/365,580 entitled "Methods for Analyzing Protein Binding Events," filed Aug. 2, 1999 (Atty Dkt No. 19501-000700);

Ser. No. 09/687,456 entitled "System and method for detecting and identifying molecular events in a test sample," filed Oct. 13, 2000 (Atty Dkt No.-12US);

Ser. No. 60/248,298 entitled "System and method for real-time detection of molecular interactions," filed Nov. 13, 2000 (Atty Dkt No.-14P);

Ser. No. 09/775,718 entitled "Bioassay device for detecting molecular events," filed Feb. 1, 2001 (Atty Dkt No.-15US);

Ser. No. 09/775,710 entitled "System and method for detecting and identifying molecular events in a test sample using a resonant test structure," filed Feb. 1, 2001 (Atty Dkt No.-16US);

Ser. No. 60/268,401 entitled "A system and method for characterizing the permittivity of molecular events," filed Feb. 12, 2001 (Atty Dkt No.-17P);

Ser. No. 60/275,022 entitled "Method for detecting molecular binding events using permittivity," filed Mar. 12, 2001 (Atty Dkt No.-18P);

Ser. No. 60/277,810 entitled "Bioassay device for detecting molecular events," filed Mar. 21, 2001 (Atty Dkt No.-19P);

What is claimed is:

1. A method for detecting a molecular or cellular event, comprising:

coupling an electromagnetic test signal in a frequency range from 1 MHz to 1000 GHz to a sample, whereby said sample interacts with and modulates said test signal to produce a modulated test signal;

detecting the modulated test signal; and analyzing said modulated test signal to detect a molecular or cellular event, wherein said coupling and detecting take place in a temperature-controlled environment, wherein said environment comprises said sample, a radiating portion of a signal-generating circuit, and a receiving portion of a signal-detection circuit and wherein said applying and detecting take place in said environment at a temperature controlled to within +0.5° C. of a desired environmental temperature, wherein the detection of the molecular or cellular event occurs in a region where both the radiating portion of the signal-generating circuit and the receiving portion of the signal-detection circuit are coupled to the sample, thereby defining a detection region.

2. The method of claim 1, wherein said temperature is controlled to within ±0.05° C. of the desired environmental temperature.

3. The method of claim 1, wherein said temperature is controlled to within ±0.00001° C. of the desired environmental temperature.

4. The method of claim 1, wherein said molecular event is binding of a ligand with an antiligand and said binding is measured without separating bound from unbound ligand.

5. The method of claim 1, wherein said radiating and receiving portions of said circuits comprise a resonant probe.

6. The method of claim 5, wherein said resonant probe comprises:

a first coaxial section comprising a longitudinally extending center conductor, a dielectric insulator disposed around the longitudinal axis of the center conductor, and an outer ground plane disposed around the longitudinal axis of the dielectric insulator, the first coaxial section having a probe head and a first gap end, the probe head comprising an open-end coaxial cross section;

a second coaxial section comprising a longitudinally extending center conductor, a dielectric insulator disposed around the longitudinal axis of the center conductor, and an outer ground plane disposed around the longitudinal axis of the dielectric insulator, the second coaxial section having a second gap end and a connecting end, the gap end comprising a open-end coaxial cross section and the connecting end comprising a coaxial connector; and a tuning element adjustably engaged between the first and second gap ends and configured to provide a variable gap distance therebetween.

7. The method of claim 5, wherein said resonant probe comprises a reentrant cavity.

8. The method of claim 1, wherein said radiating and receiving portions of said circuits comprise a non-resonant coaxial probe.

9. The method of claim 1, wherein said radiating and receiving portions of said circuits comprise a transmission line probe.

10. The method of claim 1, wherein said electromagnetic test signal comprises a signal in the electromagnetic spectrum from 10 MHz to 1000 GHz.

11. The method of claim 1, wherein said electromagnetic test signal comprises a signal in the electromagnetic spectrum from 100 MHz to 1000 GHz.

12. The method of claim 1, wherein said electromagnetic test signal comprises a signal in the electromagnetic spectrum from 100 MHz to 20 GHz.

13. The method of claim 1, wherein said coupling and detecting take place over a time period of from 2 seconds to 2 minutes for an individual sample.

14. The method of claim 1, wherein (1) multiple samples in a set of samples are coupled to electromagnetic test signals, thereby producing corresponding modulated test signals that are detected for joint analysis in order to determine one or more molecular or cellular events, and (2) coupling and detecting of all samples in said set take place in said temperature-controlled environment.

15. The method of claim 14, wherein coupling and detecting of at least two samples in said set take place concurrently.

16. The method of claim 14, wherein coupling and detecting of all samples in said set take place over a time period of from 1 minute to two hours.

17. The method of claim 1, wherein said molecular or cellular event resides in an aqueous test sample, the method further comprising:

(1) introducing a first sample into a fluid reservoir having a detection region with a volume of less than 1.0 mL, wherein the detection region resides within the receiving portion of the signal detection circuit;

(2) applying an incident test signal of greater than 10 MHz and less than 1000 GHz to the sample utilizing:

(a) a measurement probe comprising:

(A) a probe head having:

(i) a wave guide coupled to the signal generating circuit, or (ii) a transmission line, a ground plane, and a dielectric layer interposed between the transmission line and the ground plane, wherein the transmission line is coupled to the signal generating circuit;

wherein the probe head is configured to electromagnetically couple the incident test signal to the test sample within the detection region, the interaction of the incident test signal with the test sample producing a modulated test signal, the probe head further configured to recover a portion of the modulated test signal; and (B) a connecting end; and (b) a signal detector coupled to the connecting end of the measurement probe and configured to recover the modulated test signal; and (3) detecting said modulated test signal; and (4) analyzing said modulated test signal to detect said molecular or cellular event, wherein said applying and detecting take place in a temperature-controlled environment, wherein said environment comprises said sample, a radiating portion of a signal generating circuit, and a receiving portion of a signal detection circuit and wherein said applying and detecting take place in said environment at a temperature controlled to within ±0.05° C. of a desired environmental temperature.

18. The method of claim 17, wherein the molecular event is structural or functional similarity of a first molecular substance to a reference molecular substance, wherein the similarity is determined by comparing a test signal detected when the sample contains the first molecular substance to a test signal detected when the sample contains the reference molecular substance.

19. The method of claim 17, wherein the cellular event is structural or functional similarity of a first cell to a reference cell, wherein the similarity is determined by comparing a test signal detected when the sample contains the first cell to a test signal detected when the sample contains the reference cell.

20. The method of claim 17, wherein the molecular event is binding of a first molecular substance to a second molecular substance.

21. The method of claim 1, the method further comprising:

(a) introducing a first aqueous test sample into a fluid channel of a fluid transport system before coupling the electromagnetic test signal to the sample,
the fluid transport system having a fluid movement controller and the fluid channel having a sample entry end, a detection region, and a sample exit end, the detection region having a volume of less than 1 mL;

(b) causing the first sample to move through the channel from the sample entry end toward the sample exit end under the control of the fluid controller;

(c) coupling a test signal of greater than 10 MHz and less than 1000 GHz to the detection region of the fluid channel; and (d) detecting a change in the test signal as a result of interaction of the test signal with the first sample.

22. The method of claim 21, further comprising:

(e) introducing a spacer material into the channel after the first test sample, (f) introducing a further test sample into the channel after the spacer material, (g) causing the further test sample to move through the channel under the control of the fluid controller, whereby a plurality of different test samples separated by spacer material is transported through the channel without intermixing different test samples, and (f) optionally repeating steps (c)–(d) for the further test sample.

23. The method of claim 22, wherein the spacer material comprises a solution of ionic strength sufficiently high to be transported by electroosmotic pumping and the fluid movement controller utilizes electroosmotic pumping of the fluid.

24. The method of claim 22, wherein the spacer material comprises a fluid that is substantially immiscible with the test samples.

25. The method of claim 22, wherein the spacer material comprises a gaseous bubble, and the fluid movement controller utilizes physical pumping of the fluid.

26. The method of claim 21, further comprising:

providing a further fluid channel that intersects the first fluid channel in the fluidic transport system, the system providing separate control of fluid movement in the second fluid channel, the second fluid channel containing a test compound or a series of test compounds, introducing a test compound from the second fluid channel into a test sample in the first fluid channel sufficiently upstream from the test signal so that the test compound has time to bind with a molecular structure in a test sample in the first fluid channel before the test sample reaches the test signal, detecting binding by a change in the test signal.

27. The method of claim 1, wherein the molecular or cellular event is in a test sample in a detection region of a fluid reservoir, the method further comprising:

locating a measurement probe that exhibits a resonant signal response at a predefined frequency in a range from 10 MHz to 1000 GHz proximate to the detection region to electromagnetically couple a signal thereto;

supplying a reference medium to the detection region;

coupling a test signal to the detection region and recording a baseline signal response;

supplying a test sample containing or suspected of containing the molecular or cellular event to the detection region;

coupling a test signal to the detection region and obtaining a test sample response;

determining the difference, if any, between the test sample response and the baseline response; and relating the difference to the molecular or cellular event.

28. The method of claim 27, wherein the measurement probe exhibits an $S_{11}$ resonant response.

29. The method of claim 27, wherein coupling a test signal to the detection region and obtaining a baseline signal response comprises:

generating an incident signal;

coupling the incident signal to the detection region;

recovering a reflected signal from the detection region; and comparing amplitude or phase of the incident signal to amplitude or phase of the reflected signal.

30. The method of claim 29, further comprising:

storing a first test sample response; and comparing a later test sample response with the stored first test sample response.

* * * * *